US009273123B2

(12) United States Patent
Shenoy et al.

(10) Patent No.: US 9,273,123 B2
(45) Date of Patent: *Mar. 1, 2016

(54) PROTEIN A CRYSTALS AND CROSS-LINKED CRYSTALS AND METHODS OF USE THEREOF

(71) Applicant: Ajinomoto Althea, Inc., San Diego, CA (US)

(72) Inventors: Bhami Shenoy, South Grafton, MA (US); Reena Patel, Woburn, MA (US); Sibyl Baladi, Albany, NY (US); Margaret McGrath, Somerville, MA (US); Nazer Khalaf, Worcester, MA (US); Chanchal Randhawa, Malden, MA (US)

(73) Assignee: Ajinomoto Althea, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/550,807

(22) Filed: Nov. 21, 2014

(65) Prior Publication Data

US 2015/0239962 A1 Aug. 27, 2015

Related U.S. Application Data

(63) Continuation of application No. 13/395,869, filed as application No. PCT/US2010/048664 on Sep. 13, 2010, now Pat. No. 8,921,531.

(60) Provisional application No. 61/242,537, filed on Sep. 15, 2009.

(51) Int. Cl.
*C07K 16/12* (2006.01)
*C07K 1/22* (2006.01)
*C07K 14/31* (2006.01)

(52) U.S. Cl.
CPC .............. *C07K 16/1271* (2013.01); *C07K 1/22* (2013.01); *C07K 14/31* (2013.01); *C07K 2317/24* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,618,710 | A | 4/1997 | Navia et al. |
| 5,619,710 | A | 4/1997 | Travis, Jr. et al. |
| 5,976,529 | A | 11/1999 | Navia et al. |
| 6,140,475 | A | 10/2000 | Margolin et al. |
| 6,447,777 | B1 | 9/2002 | Terman et al. |
| 6,541,606 | B2 | 4/2003 | Margolin et al. |
| 8,921,531 | B2 | 12/2014 | Shenoy et al. |
| 2002/0045582 | A1 | 4/2002 | Margolin et al. |
| 2006/0030696 | A1 | 2/2006 | Bonnerjea et al. |

FOREIGN PATENT DOCUMENTS

| | | |
|---|---|---|
| CN | 1771260 A | 5/2006 |
| CN | 101120017 A | 2/2008 |
| JP | 5-508549 | 12/1993 |
| JP | 2007-525412 | 9/2007 |
| WO | WO97-36614 A1 | 10/1997 |

OTHER PUBLICATIONS

International Preliminary Report on Patentability dated Mar. 20, 2012 for PCT/US2010/048664.
JP2012-529818 Office action dated Jan. 30, 2014.
KRI0-2012-7009563 Office action dated Jan. 10, 2014.
Altschul, et al. Basic local alignment search tool. J Mol Biol. Oct. 5, 1990;215(3):403-10.
Bernstein, et al. The Protein Data Bank: a computer-based archival file for macromolecular structures. J Mol Biol. May 25, 1977;112(3):535-42.
CA2774212 Office Action dated Oct. 24, 2013.
Carter, et al. Protein crystallization using incomplete factorial experiments. J Biol Chem. Dec. 10, 1979;254(23):12219-23.
CN 201080051667.4 Office Action dated Oct. 8, 2013.
EP 10817707 Extended European Search Report dated Jun. 20, 2013.
Gilliland, et al. A Biological Macromolecule Crystallization Database: a Basis for a Crystallization Strategy. J Crystal Growth. 1988; 90:51-59.
Graille, M. et al., "Crystal Structure if a *Staphylococcus aureus* protein A domain complexted with the Fab fragment of a Human IgM antibody: Structural baise for recognition of B-cell receptors and super antigen activity," PNAS, vol. 97, Issue 10, p. 5399-5404.
International search report and written opinion dated Jan. 6, 2011 for PCT/US2010/048664.
McGinnis, et al. BLAST: at the core of a powerful and diverse set of sequence analysis tools. Nucleic Acids Res. Jul. 1, 2004;32(Web Server issue):W20-5.
McPherson. Crystallization of macromolecules: general principles. Methods Enzymol. 1985;114:112-20.
Myers, et al. Optimal alignments in linear space. Comput Appl Biosci. Mar. 1988; 4(1):11-7.
Needleman, et al. A general method applicable to the search for similarities in the amino acid sequence of two proteins. J Mol Biol. Mar. 1970;48(3):443-53.
Paut Sch, et al. Strategy for membrane protein crystallization exemplified with OmpA and OmpX. Proteins. Feb. 1, 1999;34(2):167-72.
Schelhaas, et al. Protecting group strategies in organic synthesis. Angewandte Chemie-International Edition in English. 1996; 35:2056-2083.
Shuttleworth, et al. Nucleotide sequence analysis of the gene for protein A from *Staphylococcus aureus* Cowan 1 (NCTC8530) and its enhanced expression in *Escherichia coli*. Gene. 1987;58(2-3):283-95.

(Continued)

*Primary Examiner* — Suzanne M Noakes
(74) *Attorney, Agent, or Firm* — Storella, P.C.

(57) ABSTRACT

Protein A crystals and Protein A cross-linked protein crystals (CLPCs) are described. Methods of preparing and using are also disclosed.

34 Claims, 3 Drawing Sheets

(56) References Cited

OTHER PUBLICATIONS

Sjodahl. Structural studies on the four repetitive Fe-binding regions in protein A from *Staphylococcus aureus*. Eur J Biochem. Sep. 1977;78(2):471-90.

Deisenhofer, J., "Crystallographic Refinement and Atomic Models of a Human Fc Fragment and Its Complex with Fragment B of Protein A from *Staphylococcus aureus* at 2.9- and 2.8-A Resolution", 1981, 20(9):2361-2370.

Drenth, "Principles of Protein X-Ray Crystallography", 2nd Edition, 1999 Springer-Verlag New York Inc., Chapter 1, p. 1-21.

Cudney R. Protein Crystallization and Dumb Luck. The Rigaku Journal. 1999. vol. 16, No. 1, pp. 1-7.

Polyakov et al., "Three-Dimensional Structure of *E. coli* Core RNA Polymerase: Promoter Binding and Elongation Conformations of the Enzyme", Cell, Nov. 1995, 83:365-373.

Opalka et al., "Direct localization of a Beta-subunit domain on the three-dimensional structure of *Escherichia coli* RNA polymerase", PNAS, 1999, 97(2):617-622.

Darst et al., "Insights into *Escherichia coli* RNA Polymerase Structure from a Combination of X-Ray and Electron Crystallography", Journal of Structureal Biology, 1998 124:115-122.

McPherson, A. "Current Approaches to Macromolecular Crystallization", European Journal of Biochemistry. 1990. vol. 189, pp. 1-23.

CA2774212 Office Action dated Oct. 23, 2014.

CN 201080051667.4 Office Action dated Jul. 11, 2014.

CN 201080051667.4 Office Action dated Nov. 6, 2014.

CN 201080051667.4 Office Action dated Jul. 23, 2015.

EA 201270425 Office Action dated Mar. 4, 2015.

KRI0-2012-7009563 Office action dated Sep. 24, 2014.

Morrison, SL, "Two heads are better than one". Nature Biotechnology, 2007, 25:1233-1234.

CA2774212 Office Action dated Sep. 10, 2015.

PROTEIN A CRYSTALS AND CROSS-LINKED CRYSTALS AND METHODS OF USE THEREOF

CROSS REFERENCE TO RELATED APPLICATION

This application claims the benefit of U.S. Provisional Application No. 61/242,537, filed on Sep. 15, 2009, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 14, 2015, is named ALTH-024_03US_SL.txt and is 6,440 bytes in size.

BACKGROUND

Protein A is a 40-60 kDa surface protein originally found in the cell wall of the bacteria *Staphylococcus aureus*. It has found use in biochemical research because of its ability to bind immunoglobulins. Protein A bind proteins from many mammalian species, most notably IgGs. It binds with the Fc region of immunoglobulins through interaction with the heavy chain. Recombinant Staphylococcal Protein A is often produced in *E. coli* for use in immunology and other biological research. Protein A is often coupled to other molecules such as a fluorescent dye, enzymes, biotin, colloidal gold or radioactive iodine without affecting the antibody binding site. It is also widely utilized coupled to magnetic, latex and agarose beads. Protein A is often immobilized onto a solid support and used as a reliable method for purifying total IgG from crude protein mixtures such as serum or ascites fluid, or coupled with one of the above markers to detect the presence of antibodies. Immunoprecipitation studies with protein A conjugated to beads are also commonly used to purify proteins or protein complexes indirectly through antibodies against the protein or protein complex of interest. In addition, it is widely used in purification of monoclonal antibodies from wide variety of sources.

SUMMARY OF THE INVENTION

The invention relates, in part, to the preparation of Protein A cross-linked protein crystals (CLPCs), e.g., produced so as to develop an innovative Protein A system (e.g., chromatography system) for the purification of antibodies. Protein A CLPCs offer the advantages of highly concentrated Protein A activity combined with high stability and chemical resistance. The condensed Protein A concentration reduces column size (if used), buffer volume and process time. Moreover, the cross-linking of Protein A crystals can prevent or decrease the leaching of Protein A during purification (e.g., using chromatography), e.g., of immunoglobulins (e.g., antibodies). Altogether, this can reduce antibody production time and cost.

The invention relates to crystals of Protein A and cross-linked forms ("Protein A-CLPC or CLPC") or derivatives thereof and their uses to purify immunoglobulins/antibodies or corresponding Fab or Fc fragments, e.g., polyclonal antibodies, monoclonal antibodies from cell culture, therapeutic antibodies, antibodies from bacterial culture, serum, plasma, the use of such crystals of Protein A for immunoprecipitation, and extracorporeal devices.

Disclosed herein are compositions containing a crystalline form of Protein A. An embodiment of this is a composition containing a cross-linked crystalline (CLPC) form of Protein A. In a further embodiment, the Protein A crystals are cross-linked with glutaraldehyde. In some embodiments, the Protein A crystal is cross-linked with about 0.02% to about 4% (w/v) glutaraldehyde. In yet other embodiments, the Protein A crystal is cross-linked with about 1.00% (w/v) glutaraldehyde.

The compositions disclosed herein are more active than non-crystalline forms of Protein A because they have a higher binding capacity. In an embodiment of this, the binding capacity of the crystalline forms of Protein A is at least about 100% higher than the binding capacity of the soluble immobilized form at pH 7. In yet another embodiment, the cross-linked Protein A crystal has at least about 150% of the binding capacity of the non-crystalline immobilized form of Protein A.

In an embodiment of the invention, the Protein A crystals of the invention are stable (retain their binding capacity) at about pH 2 to about pH 12.

In another embodiment the Protein A crystals disclosed herein have 0.0% protein leaching when compared to immobilized non-crystalline Protein A.

Also disclosed herein are the use of the crystalline Protein A compositions in a pre-packed column as column material, or in a membrane (impregnated), or in an extracorporeal device.

In still another embodiment of the invention, disclosed herein are kits containing the crystalline Protein A compositions disclosed herein. Such kits may contain other reagents, purification apparatus, and instructions for using the crystalline Protein A compositions described herein.

In one embodiment, crystalline Protein A can be pre-packed in a column to be used as a purification material of antibodies and antibody fragments, e.g., purification of monoclonal antibodies from mammalian cell culture, purification of monoclonal antibodies expressed in transgenic milk or polyclonal antibodies generated in serum.

Additionally disclosed are methods of producing protein crystals from recombinant soluble Protein A. Compositions, e.g., pharmaceutical compositions, including the crystals of Protein A and cross-linked forms thereof ("CLPC") are also disclosed.

In one aspect, the invention provides cross-linked Protein A crystals. The cross-linking agent can be multifunctional, and in certain embodiments, the agent is a bifunctional agent, such as glutaraldehyde. In certain embodiments, the Protein A crystals are cross-linked with glutaraldehyde at a concentration that does not substantially alter binding capacity, e.g., at a concentration of at least about 0.02% (w/v). In some embodiments, the level of cross-linking of the Protein A crystal is equivalent to that produced by treatment with 0.02% (w/v) glutaraldehyde. The level of cross-linking can be determined by methods known in the art or disclosed herein, e.g., determining the level of protein leaching.

The invention further provides Protein A crystals, e.g., protein A crystals that have a higher binding capacity, e.g., at least about 100%, 200%, 300%, 400%, 500%, or more compared to soluble Protein A.

The invention further provides a stabilized, e.g., cross-linked Protein A crystal, wherein said stabilized crystal retains a binding capacity and/or stability, in acidic conditions at least 2-, 3-fold higher than the binding capacity and/or stability retained by a soluble Protein A in similar acidic conditions (e.g., an acidic pH of about 2 to 3). In some embodiments, the stabilized Protein A crystal has at least about 200%, 300%, 400% more binding capacity and/or stability than a soluble Protein A in acidic conditions.

The invention further provides a stabilized, e.g., cross-linked, Protein A crystal, wherein said stabilized crystal retains a binding capacity and/or stability, in the presence of a protease, at least 2-, 3-fold higher than the binding capacity and/or stability retained by a soluble Protein A in similar conditions. In some embodiments, the stabilized Protein A crystal has at least about 200%, 300%, 400% more binding capacity and/or stability than a soluble Protein A in the presence of a protease. The protease can be chosen from one or more of, e.g., pepsin, chymotrypsin or pancreatin.

In other embodiments, the binding capacity of the stabilized or soluble Protein A is measured after exposing the stabilized crystal or soluble Protein A to acidic conditions and/or a protease for a predetermined length of time, e.g., at least one, two, three, four or five hours.

In a related aspect, the invention features a cross-linked, Protein A crystal which is substantially stable in variable pH conditions (e.g., about pH 2.0 or 3 to about pH 7.5 or about pH 8.5 to about pH 10-14), and/or in the presence of a protease, e.g., a protease can be chosen from one or more of the following: pepsin, chymotrypsin or pancreatin. In still other embodiments, the cross-linked crystal retains its binding capacity at least about 2-, 3-fold higher than the binding capacity retained by a soluble Protein A in acidic conditions (e.g., an acidic pH of about 2 to 3) and in the presence of a protease, as described herein. In other embodiments, the stabilized Protein A crystal is at least 200%, 300%, 400% more stable than a soluble Protein A in acidic conditions (e.g., an acidic pH of about 2 to 3) and in the presence of a protease, as described herein.

Also disclosed herein are Compositions, e.g., pharmaceutical compositions, that include the crystals and/or the cross-linked Protein A crystals.

In some embodiments, the crystals include Protein A having a sequence identical or substantially identical to Protein A sequence found in a natural source, such as *Staphylococcus aureus* or related strains. In other embodiments, the Protein A is produced by recombinant means.

In another aspect, the invention provides membranes impregnated with cross-linked protein crystals, devices, systems and methods of producing and using the same for a variety of suitable applications including, for example, the purification of antibodies and antibody fragments and removal of immunoglobulins during dialysis therapy. In this regard, the Protein A impregnated membranes of the present invention can bind to the antibodies and antibody fragments. This can effectively minimize the amount of buffer needed for purification, thus minimizing costs.

In another embodiment, the present invention provides a material including a membrane impregnated with about 3.25 mg/cm$^2$ or less of a cross-linked protein crystal. Preferably, the membranes are impregnated with cross-linked Protein A crystals ("Protein ACLPC"). The membranes impregnated with Protein A-CLPCs can be used to isolate and purify immunoglobulins and can be reused similar to immobilized Protein A.

In still another embodiment, the present invention provides a method of producing a membrane impregnated with cross-linked protein crystals, preferably Protein A-CLPC. The method includes preparing a membrane casting solution. The casting solution includes a polymeric base material, such as polyurethane, in a solvent, such as 1-methyl-2-pyrrolidinone ("NMP"), dimethylformamide ("DMF"), the like or combinations thereof. The membrane casting solution can also include a bulking agent, such as zirconium oxide, and an agent, such as polyvinylpyrrolidone ("PVP") to render the membrane more hydrophilic.

The casting solution is then mixed with a suitable amount of Protein A-CLPC, such that the membrane is impregnated with about 3.25 mg/cm$^2$ Protein A-CLPC. The solution can then be spread on a support material, such as a synthetic mesh material, and immersed into an aqueous media under suitable conditions, thus forming a membrane precipitate. The membrane precipitate is subsequently dried in a glycerol solution, preferably a mixture of glycerol and water at a ratio of 40:60.

An advantage of the present invention is to provide improved protein impregnated membranes suitable for use in a variety of different applications such as antibody purification and immunoprecipitation.

A further advantage of the present invention is to provide improved materials capable of binding antibodies without the need for any inert support unlike immobilized Protein A.

In still another aspect, the invention provides a method of reducing immunoglobulin concentration (disorder associated with elevated immunoglobulin concentration) in a subject by administering a composition, e.g., a pharmaceutical composition, that includes Protein A crystals, e.g., cross-linked Protein A crystals, as disclosed herein. In one embodiment of this aspect, the Protein A crystals are stabilized by a cross-linking agent, such as glutaraldehyde. Administration of the composition can cause a reduction of immunoglobulin concentration by at least about 10%, at least about 20%, at least about 30%, or at least about 40% or more. In some embodiments, the composition is administered orally or via an extracorporeal device. In a further embodiment, the extracorporeal device is a catheter, e.g., a catheter coated with Protein A crystals. In still another embodiment, the method of reducing immunoglobulin concentration in a mammal includes a step of assaying the immunoglobulin concentration in a biological sample of the mammal, such as a blood, plasma, or a serum sample.

In another aspect, the invention provides a composition, e.g., a pharmaceutical composition, that includes Protein A crystals, e.g., cross-linked Protein A (e.g., the crystals and/or cross-linked crystals, as disclosed herein).

In yet another aspect, the invention provides a method of treating a mammal by administering/as a sorbent in dialysis equipment (extracorporeal device) an effective amount of a pharmaceutical composition that includes Protein A crystals, e.g., cross-linked Protein A crystals (e.g., the crystals and/or cross-linked crystals, as disclosed herein).

In yet another embodiment, the crystallizing step includes concentrating the purified protein, followed by adding precipitation reagents thereby forming crystallized protein. The crystallization step can additionally include contacting the crystallized protein with a cross-linking agent, e.g., a cross-linking agent disclosed herein (e.g., glutaraldehyde). The concentration of crosslinking agent used can be in the range of about 0.01% to 20% w/v; typically, about 0.02% to 10% w/v; more typically about 0.02%, 0.5% or 1% w/v.

In other embodiments, the yield of the crystallized protein in the preparation is at least about 50%, 60%, 70%, 80% of the specific protein found in the soluble Protein A suspension. In other embodiments, the yield of the crystallized protein is at least about 90%, 95% or higher of that found in the soluble preparation. In yet other embodiments, the yield of the crystallized protein is at least about 50%, 60%, 70%, 80% of that found in the soluble preparation.

The invention further provides protein crystals, (e.g., Protein A crystals) produced by the methods disclosed herein.

In some aspects, the disclosure features Protein A crystals.

In some aspects, the disclosure features Protein A cross-linked protein crystals (CLPCs), e.g., cross-linked as described herein.

In some aspects, the disclosure features a composition containing Protein A crystals and another ingredient (e.g., buffer, e.g., Tris buffer).

In some aspects, the disclosure features a composition containing Protein A cross-linked protein crystals (CLPCs) and another ingredient (e.g., buffer, e.g., Tris buffer).

In some aspects, the disclosure features a method of making Protein A crystals, e.g., as described herein.

In some aspects, the disclosure features a method of making Protein A cross-linked protein crystals (CLPCs), e.g., as described herein.

In some aspects, the disclosure features a kit containing Protein A crystals and another component (e.g., instructions for use).

In some aspects, the disclosure features a kit containing Protein A cross-linked protein crystals (CLPCs) and another component (e.g., instructions for use).

In some aspects, the disclosure features a method of using Protein A crystals, e.g., as described herein, e.g., to purify an immunoglobulin, e.g., an antibody, e.g., a therapeutic antibody. In some embodiments, leaching of Protein A is prevented or decreased (e.g., decreased by about 10%, about 20%, about 30%, about 40%, about 50%, about 60%, about 70%, about 80%, about 90%, about 100% or about 2 fold, about 5 fold, or about 10 fold as compared to the amount of leaching when Protein A in non-crystal form is used under the same conditions.

In some aspects, the disclosure features a method of using Protein A cross-linked protein crystals (CLPCs), e.g., as described herein, e.g., to purify an immunoglobulin, e.g., an antibody, e.g., a therapeutic antibody. In some embodiments, leaching of Protein A is prevented or decreased (e.g., decreased by about 10%, about 20%, about 30%, about 40%, about 50%, about 60%, about 70%, about 80%, about 90%, about 100% or about 2 fold, about 5 fold, or about 10 fold as compared to the amount of leaching when Protein A in non-crystal form or when Protein A crystals in non-cross-linked form are used under the same conditions.

In some aspects, the disclosure features a method of using Protein A crystals, e.g., as described herein, e.g., to purify an immunoglobulin, e.g., an antibody, e.g., a therapeutic antibody. In some embodiments, binding capacity of Protein A per mL is increased (e.g., increased by about 10%, about 20%, about 30%, about 40%, about 50%, about 60%, about 70%, about 80%, about 90%, about 100% or more or about 2 fold, about 5 fold, or about 10 fold or more as compared to the amount of binding when Protein A in non-crystal form is used under the immobilized conditions (e.g., using a support).

In some aspects, the disclosure features a method of using Protein A cross-linked protein crystals (CLPCs), e.g., as described herein e.g., to purify an immunoglobulin, e.g., an antibody, e.g., a therapeutic antibody. In some embodiments, binding capacity of Protein A is increased (e.g., increased by about 10%, about 20%, about 30%, about 40%, about 50%, about 60%, about 70%, about 80%, about 90%, about 100%, or more or about 2 fold, about 5 fold, or about 10 fold or more as compared to the amount of binding when Protein A in non-crystal form or when Protein A crystals in non-cross-linked form are used under the immobilized conditions (using a support).

In some aspects, the disclosure features a column (e.g., chromatography column) containing Protein A crystals.

In some aspects, the disclosure features a column (e.g., chromatography column) containing Protein A cross-linked protein crystals (CLPCs).

In some aspects, the disclosure features a membrane (e.g., holofiber system) containing Protein A crystals.

In some aspects, the disclosure features a membrane (e.g., holofiber system) containing Protein A cross-linked protein crystals (CLPCs).

Disclosed herein are methods of crystallizing Protein A in which the Protein A is solubilized or concentrated, and to the solubilized or concentrated protein is added precipitating reagents to form crystals.

Disclosed herein are processes for the purification of immunoglobulins which include the steps of (a) mixing a medium containing immunoglobulins with a buffer solution having a pH in the range of about pH 7.0 to pH 10 and containing a combination of cations and anions to provide a buffered immunoglobulin medium; (b) contacting said buffered immunoglobulin medium with an immobilized protein A (Protein A-CLPC: Protein A is immobilized by crystallizing and cross-linking Protein A molecules) adsorbent to adsorb the immunoglobulins present in said buffered immunoglobulin medium upon said immobilized protein A adsorbent; (c) washing the Protein A-CLPC adsorbent having immunoglobulins adsorbed thereon with said buffer solution; (d) contacting said Protein A-CLPC adsorbent having immunoglobulins adsorbed thereon with a buffer solution having a pH in the range of about pH 2 to pH 6 to remove the adsorbed immunoglobulins from the Protein A-CLPC adsorbent; and (e) recovering the removed immunoglobulins in substantially pure form. In a further embodiment of this process, the process is accomplished in a column containing the crystalline compositions of Protein A described herein. In yet another embodiment of the process, the contacting of the buffered immunoglobulin medium with the Protein A-CLPC adsorbent is accomplished in a column containing Protein A-CLPC adsorbent. In another embodiment of this process, the medium containing immunoglobulins is a normal mammalian serum, or immune mammalian serum, such as plasma or ascites fluid. In other embodiments the immunoglobulin medium is obtained from a hybridoma, tissue culture fluid, cell culture fluid, a mammalian cell culture fluid, bacterial cell culture fluid, transgenic source fluid, a plant extract, or a yeast culture fluid.

In some embodiments of the process for purification, the buffer solution will have a pH in the range of about pH 7.0 to about pH 10 and the buffer is a glycine buffer, borate buffer, tris (hydroxymethyl) aminomethane buffer, or phosphate buffer. In yet other embodiments of the process of purification, the buffer solution has a concentration range of about 0.01M to about 0.25M, or about 0.05M to about 0.5M.

In still other embodiments of the process for purification, the buffer solution has a pH in the range of about pH 2 to about pH 6 and has a concentration in the range of about 0.01M to 0.25M. In some embodiments of the process of purification, the buffer solution is an acetic acid-acetate buffer and has a pH in the range of about pH 2 to about pH 6.

In another embodiment of the process for purification, the buffer solution contains potassium ions and phosphate ions in a concentration of about 1.0M to about 1.5M.

In yet another embodiment of the process for purification, the buffer solution contains ammonium ions and phosphate ions in a concentration of about 1.0M to about 1.5M. In still another embodiment of the process for purification, the buffer solution contains ammonium ions and sulfate ions in a concentration of about 1.0M to about 1.5M. In some embodiments of the process for purification the buffer solution contains sodium ions and sulfate ions in a concentration of about 1.0M to about 1.25M. In still other embodiments the buffer solution contains sodium ions, phosphate ions and chloride ions in a concentration of about 1.0M to about 1.25M.

In further embodiments of this process for purification, the immobilized Protein A adsorbent is crystalline and cross-linked Protein A without any support. In yet other embodiments the adsorbent is crystalline and cross-linked Protein A without any support attached to magnetic particles Disclosed herein is a method for purifying a protein from a contaminated solution using Protein A chromatography including the steps of: (a) adsorbing the protein to purified to an immobilized solid phase crystallized and cross-linked Protein A; (b) removing contaminants bound to the solid phase by washing the solid phase with an electrolyte solvent having a pH in the range from about 5 to about 7 and containing an electrolyte selected from the group consisting of tetramethylammonium chloride (TMAC), tetraethylammonium chloride (TEAC), tetrapropylammonium chloride and tetrabutylammonium chloride; and (c) recovering the protein from the solid. In some embodiments of this method the protein to be purified is an immunoglobulin, antibody, or fragment thereof. In still further embodiments of this method, the protein to be purified is a polyclonal antibody, monoclonal antibody, or chimeric antibody or fragment thereof. In other embodiments of this method the solid phase is a crystalline Protein A in a column or is a crystalline cross-linked Protein A in a column.

In some embodiments of the method for purifying a protein from a contaminated solution, the electrolyte solvent contains tetramethylammonium chloride (TMAC) or tetraethylammonium chloride (TEAC). In still further embodiments of this method, the concentration of the electrolyte in the electrolyte solvent is in the range from about 0.1 to about 1.0 M or in the range from about 0.25 to about 0.5 M.

In other embodiments of the method for purifying a protein from a contaminated solution, the contaminants are Chinese Hamster Ovary Proteins (CHOP). In some embodiments of this method the contaminated solution comprises Harvested Cell Culture Fluid (HCCF) comprising a recombinant antibody.

In embodiments of the method for purifying a protein from a contaminated solution, the elution buffer of step (c) involves eluting the protein using an elution buffer having a pH in the range from about 2.0 to about 5.0 or from about 2.5 to about 3.5.

Disclosed herein is a method for purifying a protein which has been produced a produced by a Chinese Hamster Ovary (CHO) cell using Protein A chromatography including the steps of: (a) adsorbing the protein to Protein A immobilized which is done by crystallizing and crosslinking of Protein A to create a solid phase; (b) removing Chinese Hamster Ovary Protein (CHOP) contaminants bound to the solid phase by washing the solid phase with an electrolyte solvent comprising an electrolyte selected from the group consisting of tetramethylammonium chloride (TMAC), tetraethylammonium chloride (TEAC), tetrapropylammonium chloride and tetrabutylammonium chloride; and (c) recovering the protein from the solid phase.

Also disclosed herein is a method for purifying a protein that has been produced by a Chinese Hamster Ovary (CHO) cell using Protein A chromatography including the steps of: (a) adsorbing the protein to Protein A immobilized which was done by crystallizing and cross-linking to create a solid phase; (b) removing Chinese Hamster Ovary Protein (CHOP) contaminants bound to the solid phase by washing the solid phase with an electrolyte solvent having a pH in the range from about 5 to about 7 and containing an electrolyte solvent selected from the group consisting of tetramethylammonium chloride (TMAC), tetraethylammonium chloride (TEAC), tetrapropylammonium chloride and tetrabutylammonium chloride, wherein the concentration of the electrolyte in the electrolyte solvent is in the range from about 0.25 to about 0.5 M; and (c) recovering the protein from the solid phase.

Disclosed herein is a method of treating a disorder associated with elevated immune globulins concentration in a mammal, the method comprising administering Protein A crystals to the mammal in an amount sufficient to reduce one or more symptoms associated with the disorder. In some embodiments of this method, the disorder is related to immune function.

Disclosed herein is a method of producing a membrane, the method includes the steps of: (a) preparing a casting solution composed of a polymeric base material in a solvent; (b) adding a sufficient amount of a cross-linked protein crystal to the casting solution; (c) applying the membrane casting solution to a support material; (d) immersing the membrane casting solution and the support material in an aqueous media; (e) forming a membrane composite material; (f) and drying the membrane composite material with a fluid medium. In some embodiments of this method the polymeric base material is composed of a suitable polymer including polyurethane. In yet other embodiments of this method, the cross-linked protein crystal includes a protein selected from the group consisting of Protein A, Protein G, Protein L and combinations thereof. In still other embodiments of this method, the solvent is selected from the group consisting of 1-methyl-2-pyrrolidinone, dimethylformamide and combinations thereof. In some embodiments of this method the fluid medium includes glycerol.

Disclosed is a method of producing a Protein A impregnated membrane, including the steps of: (a) forming a membrane casting solution including polyurethane and a bulking agent in a solvent; (b) adding the Protein A-CLPC to the membrane casting solution; (c) processing the membrane casting solution in an aqueous media; (d) and forming a membrane precipitate impregnated with the Protein A-CLPC. In some embodiments of this method the bulking agent is selected from the group consisting of zirconium oxide, zirconium phosphate, carbon and combinations thereof. In another embodiment the method of producing an impregnated membrane includes the additional step of drying the membrane precipitate with a glycerol solution.

Disclosed herein is a material capable of removing immunoglobulins from dialysate or body fluids during dialysis therapy, the material including a membrane impregnated with cross-linked protein crystal wherein the membrane has been dried with a fluid medium. In an embodiment of this method the cross-linked protein crystal includes a protein selected from the group consisting of Protein A, Protein G, Protein L and combinations thereof. In still further embodiments the membrane includes a bulking agent selected from the group consisting of zirconium oxide, zirconium phosphate, carbon and combinations thereof. In still other embodiments of this method, the fluid medium includes glycerol.

Disclosed herein is a device for removing immunoglobulins from a dialysate or body fluid used during dialysis therapy, wherein the device includes: a body defining an interior with an inlet and an outlet, the interior containing a layer of a membrane impregnated with a cross-linked protein crystal wherein the membrane has been dried with a fluid medium. In some embodiments of this device, the cross-linked protein crystal includes a protein selected from the group consisting of Protein A. Protein G Protein L and combinations thereof. In other embodiments of this device the fluid medium includes glycerol.

Disclosed herein is a system for providing dialysis therapy, the system comprising a device capable of removing immunoglobulins during dialysis, wherein the device includes a body defining an interior with an inlet and an outlet, and the interior contains a layer of a membrane impregnated with cross-linked protein crystal wherein the membrane has been dried with a fluid medium. In embodiments of this system the cross-linked protein crystal includes a protein selected from the group consisting of Protein A, Protein G, Protein L and combinations thereof. In other embodiments the fluid medium includes glycerol.

Disclosed herein is a method of providing dialysis therapy, the method including the steps of: (a) passing a dialysis fluid or body fluid through a device including a layer of a membrane impregnated with cross-linked protein crystal wherein the membrane has been dried with a glycerol solution; and (b) removing a therapeutically effective amount of immunoglobulins from the dialysis fluid or body fluids. In an embodiment of this method, the cross-linked protein crystal includes a protein selected from the group consisting of Protein A, Protein U Protein L and combinations thereof.

Disclosed herein are compositions including crystalline form of Protein A. In some embodiments the source of Protein A is from *Staphylococcus aureus* strains. In still other embodiments the Protein A is produced by recombinant means or is chemically synthesized. In some embodiments the Protein A has a full length native protein sequence. In still other embodiments, the Protein A contains at least one antibody binding domain. In yet other embodiments, the Protein A is chemically modified. In other embodiments the Protein A has a mutation or is a functional derivative of a native Protein A.

Disclosed herein are compositions including cross-linked crystalline form of Protein A. In some embodiments the composition is cross-linked with glutaraldehyde.

Disclosed herein is a method of purifying an immunoglobulin including the step of binding said immunoglobulin to a composition including crystalline form of Protein A and/or cross-linked crystalline form of Protein A. In some embodiments the immunoglobin is an antibody, a monoclonal antibody, a Fab fragment, a Fc fragment, a single chain antibody, a chimeric antibody, a fully human antibody, or a humanized antibody. In other embodiments the immunoglobulin belongs to class IgG. In still other embodiments of this method the immunoglobulin is chemically modified.

Disclosed herein is a method of making crystalline form of Protein A using the hanging-drop vapor diffusion crystallization method or batch crystallization method including the steps of: (a) placing Protein A in deionized water at a 1:1 protein reagent ratio, wherein said reagent is selected from the group consisting of a composition containing 2 M ammonium sulfate, 0.1 M cacodylate buffer pH 6.5 and 0.2 M NaCl; 2 M ammonium sulfate in citrate buffer pH 5.5; 1 M sodium citrate, 0.1 M Tris-HCl buffer pH 7, and 0.2 M NaCl; 0.8 M $NaH_2PO_4$/1.2 M $K_2PO_4$ in 0.1 M acetate buffer pH 4.5; and 2 M ammonium sulfate, Tris-HCl buffer pH 7 and 0.2 M lithium sulfate; and (b) incubating until crystals appear. In some embodiments of this method the Protein A in step (a) is at concentration of about 10 mg/ml or about 300 mg/ml Protein A in deionized water. In still other embodiments of this method, the Protein A in step (a) is at concentration of about 50 mg/ml or about 120 mg/ml Protein A in deionized water.

Dosclosed herein is a method of making cross-linked crystalline form of Protein A comprising mixing crystalline form of Protein A with glutaraldehyde. In some embodiments of this method, the glutaraldehyde is at a final concentration of about 0.2 to about 4%. In other embodiments of this method the glutaraldehyde is at a final concentration of about 1%

All publications, patent applications, patents, and other references mentioned herein are incorporated by reference in their entirety. In the case of conflict, the present specification, including definitions, controls. In addition, the materials, methods, and examples are illustrative only and not intended to be limiting.

The details of one or more embodiments of the invention are set forth in the accompanying drawings and the description below.

DETAILED DESCRIPTION

Figure 1:
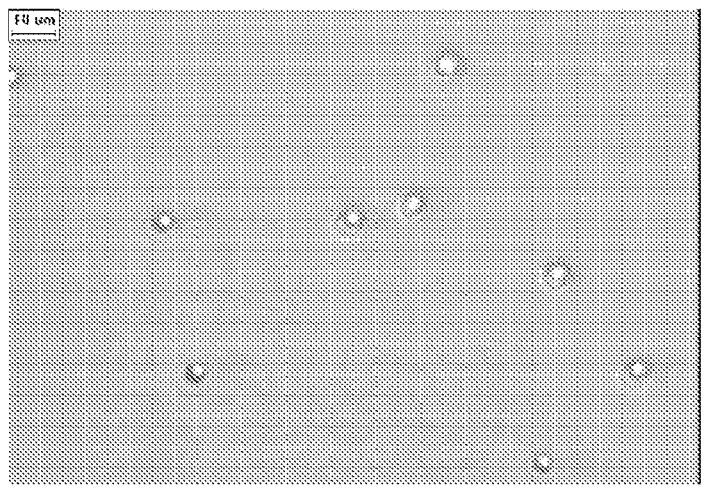
FIG. 1. Protein A crystals in hanging drop. Recombinant Protein A (120 mg/ml in DI $H_2O$) was crystallized in hanging drops with Wizard II crystallization screen.

The present invention relates to compositions comprising crystalline Protein A and cross-linked Protein A, and methods of making and using such crystalline compositions for separating an immunoglobulin/antibodies or an Fc-fragment, Fab fragment, single-chain antibodies and monoclonal antibodies from microorganisms, serum, plasma, mammalian cell culture. The crystalline compositions described herein have the ability of binding at least one immunoglobulin through the Fc-portion of the latter, from a liquid containing the immunoglobulins in a mixture of other substances.

Without wishing to be bound by any particular theory, the invention is characterized in that the liquid containing said immunoglobulin/antibodies is contacted with a solid phase consisting of crystalline cross-linked Protein A substance which is insoluble in said liquid and which has at least one or more immunoglobulin or its Fc-fragment binding regions thereto. The Fc-part of the immunoglobulin or the Fc-fragment is able to bind the Protein A-CLPC so that said Protein A-CLPC is bound to the Fc-part of said immunoglobulin/ antibody or to the Fc-fragment but not the contaminating substances in the liquid, whereupon the liquid with the remaining contaminants is separated from the solid phase and the bound antibodies is optionally also separated from said solid phase.

The method of the present invention distinguishes from known methods used for the same purpose in that it avoids complicated multistage operations using, inter alia, ion exchange chromatography and also additional solid support such as agarose etc. By means of the new method, the immunoglobulin/antibody/fragments in question is obtained in surprisingly pure form in a very simple manner under convenient conditions and with a high yield. The Protein A-CLPC in question is extremely valuable since it is able to reversibly bind immunoglobulins specifically with a very high binding capacity when compared to conventional immobilized Protein A because the bond is effected at the Fc-part of the immunoglobulin.

The immunoglobulin in question can derive from different animal species, primarily vertebrates, preferably mammals.

As is known, immunoglobulins may belong to different immunoglobulin classes, such as class A (IgA), D (IgD), E (IgE), G (IgG) and M (IgM). One valuable aspect of the invention is that it can be applied in connection with Protein A-CLPC capable of binding themselves to immunoglobulins belonging to the IgG class, since this class, inter alia, quantitatively dominates among the immunoglobulins. The Fc-part of immunoglobulins can be split off therefrom by known enzymatic methods, whereby free Fc-fragments are obtained. The Fc-part of a specific immunoglobulin is often structurally similar in different animal species. Since, for example, Protein A from *S. aureus* reacts with the Fc-part of IgG, the method of the present invention often enables IgG from different animal species to replace one another.

According to the invention, the polypeptide (Protein A-CLPC) may be the so-called protein A from *Staphylococcus aureus* or fragments of said protein, said fragments being of a polypeptide nature and having the ability of binding at least one immunoglobulin at the Fc-part of the latter. Said polypeptides (protein A and fragments) deriving from *S. aureus* can bind immunoglobulins belonging to the IgG-class at their Fc-parts. Other examples are polypeptides from *Staphylococcus epidermidis* and from other bacteria strains.

In accordance with the invention, there should be used when practicing the method a protein A-CLPC (polymeric substance) insoluble in the liquid, whereby the polymeric substance has at least one immunoglobulin or its Fc-fragment binding region thereto. The Protein A-CLPC can thus not be dissolved out of the solid phase or removed therefrom during washing operations. Preferably, the Protein A-CLPC is formed by cross-linking of protein A crystals by means of bonds of a covalent nature.

The Protein A-CLPC can be used in a column consisting of cross-linked Protein A in crystalline particulate form which is pre-packed in columns that provide for easy affinity purification of polyclonal antibodies, monoclonal antibodies, Fab fragments from various sources. The crystalline cross-linked Protein A is prepared using a cross-linking method that results in excellent protein stability and binding characteristics. The columns are intended for traditional gravity-flow procedures.

Alternatively, the Protein A-CLPC can be bound to the polymer (solid surface) or magnetic particles by means of methods conventionally used when binding polypeptides, e.g., proteins, to polymeric substances, e.g. by means of cyanogen halide, isocyanates etc. The insoluble polymeric substances used may be such as are generally available for similar purposes, i.e., polymers with functional groups which can be used when binding proteins to polymers. Examples of such functional groups are hydroxyl groups, mercapto groups, primary and secondary amino groups, carbonyl groups, hydrazide groups, diazo groups and carboxyl groups. These groups can be used when forming bridges by conventional methods from the polymer to a protein, which in this case is the Protein A-CLPC. The polymer, which is insoluble in the liquid used, may, however, swell in said liquid. For example, it may swell in water when an aqueous liquid is used. The polymer may consist of a three-dimensional network obtained, for example, by cross-linking a polymer such as a polysaccharide. Thus, very different polymers can be used, for example, cellulose, agarose, polyaminostyrene, cross-linked polymers (for example cross-linked polysaccharides such as dextran cross-linked with epichlorohydrin (Sephadex®) or with diepoxides (for example with 1,4-butanediol diglycide ether)) or starch or cellulose derivatives or polyvinyl alcohol cross-linked with epichlorohydrin or diepoxides. Other examples are insoluble polymers obtained by reacting tetraethylenepentamine or hexamethylenediamine with epichlorohydrin or diepoxides. Another example is cross-linked polyacrylamide polymer substituted by p-aminophenyl groups (Enzacryl®).

The solid phase may exist in crystalline cross-linked Protein A or embedded in polymeric substance or membrane. In many instances it may be suitable to use the Protein A in particulate form. Other examples include a polymeric test tube wall to which is bound a Protein A-CLPC to purify immunoglobulin or its Fc-fragment, e.g., IgG or its Fc-fragment.

The substances from which the relevant immunoglobulin/antibody/fragments is separated by the method described herein may be of widely differing character. Thus, such immunoglobulins may be purified away from polypeptides (e.g., proteins), polysaccharides, nucleic acids or low molecular weight substances from the microorganisms from which the relevant antibody was produced.

The method of the present invention is carried out in the presence of a liquid. The liquid used is primarily an aqueous liquid, e.g., an aqueous buffered NaCl solution having a suitable pH, e.g., in the proximity of the neutral point.

The relevant antibodies/fragments thereof bound to the Protein A-CLPC in accordance with the invention may readily be released from the CLPC under mild conditions, e.g., by changing the pH or ion strength.

Crystals of Protein A (Protein A-CLPC) as described herein can bind antibodies or its Fab fragments and can be used in purification or in immunology or immunoprecipitation studies from various sources without the need for any solid support. Crystals of Protein A (Protein A-CLPC) can also reduce immune circulating complexes or IgG from plasma by immunoadsorption in an extracorporeal device in a mammal. Methods of using Protein A/CLPC crystals to purify antibodies are described herein. Additionally, Protein A crystals and cross-linked crystals (CLPCs) are provided, as are compositions comprising and using the same. Additionally disclosed are methods of producing large quantities of protein crystals/CLPCs from soluble form of Protein A.

Definitions. In order that the present invention may be more readily understood, certain terms are first defined. Additional definitions are set forth throughout the detailed description.

As used herein "Whole Antibody or Antibody Fragment" means a whole antibody or antibody fragment, e.g., a single-chain Fv fragment or Fab antibody fragment, according to this invention, is a functional antibody or antibody fragment, i.e., that is able to recognize and bind to its specific antigen in vitro or in vivo, and may initiate any subsequent actions associated with antibody-binding, e.g., Direct Cytotoxicity, Complement-Dependent Cytotoxicity (CDC), Antibody-Dependent Cytotoxicity (ADCC).

The term "Antibody" means a glycoprotein of approximate MW 150 kD, that is produced by the humoral arm of the immune system of vertebrates in response to the presence of foreign molecules in the body. Antibodies are essential for the prevention and resolution of infection by microorganisms, e.g. parasites, bacteria and viruses. Antibodies perform this function by recognizing and binding, in a highly specific manner, protein (or, sometimes, other organic molecules including polysaccharides, glycoproteins, lipids, or nucleic acids) configurations called antigens (or epitopes), including those on invading microorganisms and their products. Antibodies bind their target antigens through highly specific interactions between hypervariable domains, called antigen-binding sites, on the antibody, and the epitope itself. Upon binding to the antigen, antibodies activate one or more of the many effector systems of the immune system that contribute to the neutralization, destruction and elimination of the infecting microorganism, or other antigen-containing entity, e.g. cancer cell.

Antibodies are also used for the treatment of cancer, inflammation, cardiovascular disease, and transplant rejection, by virtue of their specific binding and subsequent neutralization of the cellular targets, which are involved in disease states. For example, monoclonal antibody Infliximab binds to tumor necrosis factor and neutralizes its role in inflammation by blocking its interaction with cell surface receptor, while Rituximab targets malignant B lymphocytes by binding to their cell surface CD20 antigen.

A single antibody molecule has a structure composed of two identical heavy chains (each of approximate MW 50 kD) covalently bound to each other, and two identical light chains (each of approximate MW 25 kD), each covalently bound to one of the heavy chains. The four chains are arranged in a classic "Y" motif. The bottom "leg" of the "Y" is called the Fc region ("c" stands for "crystallizable" or, alternatively, "complement-binding") and is used to anchor the antibody within cell membranes, and also to bind macrophage cells and activate complement. The two "arms" at the top of the "Y" are called Fab regions (the "ab" stands for "antigen-binding"). Each Fab region contains a constant region (at the juncture of the Fab and the Fc regions) and a variable region (which extends to the tip of the "Y"). Each variable region contains identical antigen-binding sites (at regions within the variable regions called "hypervariable" regions) at each tip of the "Y". Thus, each Fab region has one antigen-binding site, and the complete antibody molecule therefore has two antigen-binding sites (i.e., is "bivalent"). The two antigen-binding sites on a naturally occurring antibody are identical to each other, and therefore the antibody is specific for one antigen (i.e., is "monovalent").

A number of molecular fragments of antibody molecules have been isolated to date. These do not occur naturally, but are engineered from one or more complete antibody molecules. These fragments include Fab fragments (a single Fab that is isolated from a complete antibody by digestion with the enzyme papain), and F(ab')$_2$ fragments (two Fabs covalently-bound to each other, produced by digesting the antibody with the enzyme pepsin). Fab fragments are monospecific, while F(ab')$_2$ fragments are bispecific. Recently, a number of engineered antibody fragments have been introduced. These include double-stranded Fv (dsFv) fragments and single-chain Fv (scFv) fragments (the "v" stands for "variable" in both cases). A dsFv fragment consists of an Fab fragment minus the constant regions, i.e., consisting only of the variable regions of a heavy and light chain covalently bound to each other. A scFv fragment is a single polypeptide chain, consisting of the variable region of a heavy chain linked via a peptide linker to the variable region of a light chain. Classically, both dsFv and scFv fragments are monovalent (and thus mono-specific). However, two dsFv fragments or two scFv fragments can themselves be linked to form a bispecific fragment (which would be analogous to an F(ab')$_2$ fragment without the constant regions). Furthermore, it is possible to link two dsFv fragments or scFv fragments with different antigen-binding sites (i.e., different specificities), to form a bispecific fragment. Such fragments may be used as either research tools or therapeutic or diagnostic reagents.

There are five classes of antibodies (also called immunoglobulins) in humans: IgG, IgM, IgA, IgD, and IgE, each with its own unique characteristics and function. IgG, IgD, and IgE are all made up of one antibody molecule, while IgA can be made up of one, two or three such molecules and IgM consists of five. Furthermore, in humans, there are four subclasses of IgG (IgG1, IgG2, IgG3, or IgG4), and two subclasses each of IgM and IgA (1 and 2, respectively). For example, the monoclonal antibody Rituximab (Rituxan™) is an IgG1 antibody.

Though naturally occurring antibodies are derived from a single species, engineered antibodies and antibody fragments may be derived from more than one species of animal, i.e., may be chimeric. To date, mouse (murine)/human chimeric antibodies have been generated, though other species' combinations are possible. Chimeric antibodies have been further broken down into two subtypes: chimeric and humanized. Chimeric murine/human antibodies contain approximately 75% human and 25% mouse amino acid sequences, respectively. The human sequences represent the constant regions of the antibody while the mouse sequences represent the variable regions (and thus contain the antigen-binding sites) of the antibody. The rationale for using such chimeras is to retain the antigen specificity of the mouse antibody but reduce the immunogenicity of the mouse antibody (a murine antibody would cause an immune response against it in species other than the mouse) and thus be able to employ the chimera in human therapies. Chimeric antibodies also include those which comprise CDR regions from different human antibodies. CDR regions, also called hypervariable regions, are sequences within the variable regions of antibody molecules that generate the antigen-binding sites. CDR regions are so-named because the binding site is complementary in shape and charge distribution to the epitope recognized on the antigen.

Alternatively, chimeric antibodies comprise framework regions from one antibody and CDR regions from another antibody. Chimeric antibodies also include those which comprise CDR regions from at least two different human antibodies. Humanized antibodies contain approximately 90% (or more) human amino acid sequences. The only murine sequences present are those for the hypervariable region (that are the actual antigen-binding sites contained within the variable region). Humanized antibodies have minimal mouse immunogenicity as compared with chimeric antibodies.

There are generally two types of antibodies that can be distinguished by their specificities: polyclonal antibodies and monoclonal antibodies. Polyclonal antibodies are those that are found as the immunoglobulin fraction of blood, and are essentially a polyclonal mixture of many different types of antibodies specific for the different antigens the individual has been exposed to (i.e., they originate from many different clones of B lymphocytes (or B cells), the cell that produces antibodies).

Monoclonal antibodies are antibodies of a single specificity, i.e., that are derived from a single clone of B lymphocytes (B cells). These antibodies have exquisite specificity for their target antigens and also can be produced in high amounts (i.e., high titres). They are useful as markers for specific antigens (e.g., cancer antigens), as diagnostic agents (e.g., in assays to detect viruses like HIV-1), and as therapeutic agents. Whole monoclonal antibodies are those that have a classic molecular structure that includes two complete heavy chains and two complete light chains. This is distinguished from antibody fragments, such as Fab, F(ab')$_2$, Fc fragments, dsFv fragments, and scFv fragments.

Traditionally, monoclonal antibodies have been produced by fusing the antibody-producing B cell with an immortal hybridoma cell to generate B cell hybridomas, which continually produce monoclonal antibodies in cell culture. Another method that is traditionally used to generate monoclonal antibodies involves the expression of the monoclonal antibodies in bacterial cell culture using phage-display technology. Currently, however, monoclonal antibodies may be produced in vivo in large quantities in genetically-modified animals, such as cows and goats (Genzyme Transgenics), pigs and rabbits (Medarex, PPL Therapeutics), and chickens (Tranxenogen), and in plants, such as tobacco and corn (Epicyte, Integrated Protein Technologies, Meristem Croptech, and others). For example, large amounts of monoclonal antibodies can be found in the milk of genetically-modified goats (Genzyme Transgenics). Protein A-CLPC can be used to purify antibodies from all such sources according to this invention. Furthermore, as a result of transgenics, mice have been modified to contain and express the entire human B cell genome (which encodes human antibodies). Therefore, such transgenic mice (Abgenix) are a source of human antibodies can be purified using Protein A-CLPC according to this invention. It should be noted that glycosylation is specific to the animal that is producing the antibodies. For example, human antibodies from sources other than humans will have subtly different glycosylation profiles. Therefore, the whole antibodies or single-chain Fv antibody fragments or Fab antibody fragments of this invention may display modified glycosylation or be deglycosylated. Antibodies which can be purified using Protein A-CLPC according to this invention also include derivatized antibodies. Such antibodies include those derivatized with polyethylene glycol or at least one carbohydrate moiety or least one methyl or ethyl group.

Clinically relevant antibodies may also be classified according to the therapeutic area in which they are to be employed. Such antibodies include, for example, those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. Such antibodies also include antibodies for radioimmunotherapy. Antibodies which may be purified according to the present invention include, for example, Abciximab, Palivizumab, Murumonab-CD3, Gemtuzamab, Trastuzumab, Basiliximab, Daclizumab, Etanercept and Ibritumomab tiuxetan.

As used herein "Aqueous-organic solvent mixture"—means a mixture comprising n % organic solvent, where n is between 1 and 99 and m % aqueous, where m is 100-n As used herein "Biocompatible polymers" means polymers that are non-antigenic (when not used as an adjuvant), non-carcinogenic, non-toxic and which are not otherwise inherently incompatible with living organisms. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly ($\beta$-hydroxybutryate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

As used herein "Biodegradable polymers" means polymers that degrade by hydrolysis or solubilization. Degradation can be heterogenous—occurring primarily at the particle surface, or homogenous—degrading evenly throughout the polymer matrix.

As used herein, a "biological sample" is biological material collected from cells, tissues, organs, or organisms, for example, to detect an analyte. Exemplary biological samples include a fluid, cell, or tissue sample. Biological fluids include, for example, serum, blood, plasma, saliva, urine, or sweat. Cell or tissue samples include biopsy, tissue, cell suspension, or other specimens and samples, such as clinical samples.

As used herein, a Co-polymer means a polymer made with more than one monomer species.

As used herein, an Emulsifier is a surface active agent which reduces interfacial tension between polymer coated crystals and a solution.

A "crystal" is one form of the solid state of matter, comprising atoms arranged in a pattern that repeats periodically in three dimensions (see, e.g., Barret, Structure of Metals, $2^{nd}$ ed., McGraw-Hill, New York (1952)). A crystal form of a polypeptide, for example, is distinct from a second form—the amorphous solid state. Crystals display characteristic features including shape, lattice structure, percent solvent, and optical properties, such as, e.g., refractive index.

As used herein a "Cross-linked crystal form of protein have the property that the cross-linked protein crystals remain insoluble and in the solid state when added to solution.

An "extracorporeal device" is a structure that is not within the body for bringing a body fluid in contact with Protein A crystals in the treatment of an individual. Preferably, an extracorporeal device is a device used for dialysis, including kidney dialysis, a device for continuous arteriovenous hemofiltration, an extracorporeal membrane oxygenator, or other device used to filter waste products from the bloodstream. Similarly, components of devices to filter waste products are encompassed by the term, including a tube, a porous material, or a membrane, for example. In particular, an extracorporeal device may be a dialysis device. It may also be a membrane of a dialysis device.

A "functional fragment" of Protein A is a portion of a Protein A polypeptide that retains one or more binding activities towards antibodies or its FAb fragments of Protein A, such as the ability to be used in purification of antibodies. As used herein, a functional fragment may comprise terminal truncations from one or both termini, unless otherwise specified. For example, a functional fragment may have 1, 2, 4, 5, 6, 8, 10, 12, 15, or 20 or more residues omitted from the amino and/or carboxyl terminus of a Protein A polypeptide. Preferably, the truncations are not more than 20 amino acids from one or both termini. A functional fragment may optionally be linked to one or more heterologous sequences or mutations to any amino acids in the original native sequence of Protein A.

The term "individual" or "subject" refers to any mammal, including but not limited to, any animal classified as such, including humans, non human primates, primates, baboons, chimpanzees, monkeys, rodents (e.g., mice, rats), rabbits, cats, dogs, horses, cows, sheep, goats, pigs, etc.

Insoluble and stable form of a protein. A form of a protein which is insoluble in aqueous solvents, organic solvents or aqueous-organic solvent mixtures and which displays greater stability than the soluble form of the protein. According to an alternate embodiment of this invention, the phrase "insoluble and stable form of a protein" may be a protein which is insoluble in dry and wet formulations. In any embodiment, the cross-linked protein crystals may be active in insoluble form.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80% 90% (w/w) pure, even more preferably, 90 to 95% pure; and, most preferably, at least 95%, 96%, 97%, 98%, 99%, 99.5%, 99.8% or 100% (w/w) pure.

As used herein, the term "about" refers to up to ±10% of the value qualified by this term. For example, about 50 mM refers to 50 mM±5 mM; about 4% refers to 4%±0.4%.

As used herein, "macromolecular substrate" means a large biomolecule, such as a protein or a carbohydrate having a molecular weight of at least 600-700 Daltons, which is also a substrate for a reaction catalyzed by the protein constituent of a cross-linked protein crystal.

The term "Organic solvents" means any solvent of non-aqueous origin.

The protein constituents of the cross-linked protein crystal formulations of this invention may be naturally or synthetically modified. They may be glycoproteins, unmodified proteins or contain other modifications.

As used herein, "Protein activity", means an activity selected from the group consisting of binding, catalysis, or activities which generate a functional response within the environment in which the protein is used, such as the binding of immunoglobulins, immunoprecipitation, or combinations thereof.

The term "soluble form of protein" means individual protein molecules in solution and dissociated from a crystal lattice.

The terms "therapeutically effective dose," or "therapeutically effective amount," refer to that amount of a compound that results in prevention, delay of onset of symptoms, or amelioration of symptoms of an immune-related condition, such as adult thrombocytopenic purpura. A therapeutically effective amount will, for example, be sufficient to treat, prevent, reduce the severity, delay the onset, and/or reduce the risk of occurrence of one or more symptoms of a disorder associated with elevated immunoglobulins/IgGs or its sub-classes concentrations. The effective amount can be determined by methods well known in the art.

The terms "treatment." "therapeutic method," and their cognates refer to treatment of an existing disorder and/or prophylactic/preventative measures. Those in need of treatment may include individuals already having a particular medical disorder, as well as those at risk or having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder.

The term "Polymer" means a large molecule built up by the repetition of small, simple chemical units. The repeating units may be linear or branched to form interconnected networks. The repeat unit is usually equivalent or nearly equivalent to the monomer.

Polymeric carriers as used herein mean polymers used for encapsulation of Protein A-CLPC for purification or for delivery of such Protein A-CLPC, including biological delivery. Such polymers include biocompatible and biodegradable polymers. The polymeric carrier may be a single polymer type or it may be composed of a mixture of polymer types. Polymers useful as the polymeric carrier, include for example, poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutryate), poly (caprolactone) and poly (dioxanonc); poly (ethylene glycol), poly ((hydroxypropyl)methacrylamidc, poly [(organo)phosphazene], poly (ortho esters), poly (vinyl alcohol), poly (vinylpyrrolidone), maleic anhydride-alkyl vinyl ether copolymers, pluronic polyols, albumin, natural and synthetic polypeptides, alginate, cellulose and cellulose derivatives, collagen, fibrin, gelatin, hyaluronic acid, oligosaccharides, glycaminoglycans, sulfated polysaccharides, modified starches such as amylose starch, amylopectin starch, hydroxyethyl starch, methacrylate starch, and other starches, and any conventional material that will encapsulate protein crystals.

As used herein, Protein A refers to a polypeptide from *Staphylococcus aureus* strains. Protein A are a group of polypeptides known in the art capable of binding immunoglobulin or its Fc-fragments. Protein A is a cell wall component produced by several strains of *Staphylococcus aureus* that consists of a single polypeptide chain of molecular weight 42,000 and contains little or no carbohydrate. It consists of six regions, five of which bind IgG. Protein A binds specifically to the Fc region of immunoglobulin molecules, especially IgG. The Protein A molecule contains four high affinity ($Ka=10^8/M$) binding sites capable of interacting with the Fc region of several species. The molecule is heat-stable and retains its native conformation when exposed to denaturing reagents such as 4 M urea, 4 M thiocyanate and 6 M guanidine hydrochloride.

Immobilized Protein A has been used extensively for the isolation of IgG from several species of mammals. However, the interaction between Protein A and IgG is not equivalent for all species. Even within a species, Protein A interacts with some subgroups of IgG and not others. For instance, human $IgG_1$, $IgG_2$ and $IgG_4$ bind strongly, whereas $IgG_3$ does not bind and mouse $IgG_1$ binds poorly to Protein A. There are also many instances in which monoclonal antibodies do not bind to Protein A such as the majority of rat immunoglobulins. Despite its variable binding characteristics, Protein A possesses IgG binding properties that make it ideal for affinity purification of IgG. One molecule of immobilized protein A can bind at least two molecules of IgG.

Another protein, Protein G, a cell surface protein from Group G *Streptococci*, is a type III Fc receptor and binds IgG with a non-immune mechanism similar to that of protein A. A recombinant form of the protein produced in *E. coli*, from which the albumin-binding region of the native protein has been genetically deleted, can also be used for purification of IgGs. Recombinant protein G contains two Fc-binding regions.

Another antibody binding protein, Protein L, is a cell surface protein of bacterial species *Peptostreptoccus magnus* and is found to bind Ig through L chain interaction. It consists of 719 amino acid residues. The molecular weight of Protein L purified from the cell walls of *Peptostreptoccus magnus* was first estimated as 95 kD by SDS-PAGE in the presence of reducing agent 2-mercaptoethanol, while the molecular weight was determined to be 76 kD by gel chromotography in the presence of 6 M guanidine HCl. Unlike Protein A and Protein G which bind to the Fc region of immunoglobulins (antibodies), Protein L binds antibodies through light chain interactions. Since no part of the heavy chain is involved in the binding interaction, Protein L binds a wider range of antibody classes than Protein A or G. Protein L binds to representatives of all antibody classes, including IgG, IgM, IgA, IgE and IgD. Single chain variable fragments (ScFv) and Fab fragments also bind to Protein L. Protein L binding is restricted to those antibodies that contain kappa light chains. Given the specific requirements for effective binding, the main application for immobilized Protein L is purification of monoclonal antibodies from ascites or cell culture supernatant that are known to have the kappa light chain.

The present invention has applicability to isoforms of Protein A, and glycoforms of those isoforms.

Protein A is used to prepare the crystals which are used in methods described herein. Protein A may be isolated, for example, from a natural source, or may be derived from a natural source. As used herein, the term "derived from" means having an amino acid or nucleic acid sequence that naturally occurs in the source. For example, Protein A derived from *Staphylococcus aureus* will comprise a primary sequence of a *Staphylococcus aureus* Protein A polypeptide, or will be encoded by a nucleic acid comprising a sequence found in *Staphylococcus aureus* that encodes an Protein A or a degenerate thereof. A protein or nucleic acid derived from a source encompasses molecules that are isolated from the source, recombinantly produced, and/or chemically synthesized or modified. The crystals provided herein may be formed from polypeptides comprising amino acid sequences of Protein A, or a functional fragment of Protein A that retains antibody binding region(s). Preferably, the Protein A retains at least one functional binding characteristic of a naturally occurring Protein A, e.g., retains one or more of the ability to bind at least one antibody.

Protein A has been previously isolated and are thus available from many strains of *Staphylococcus aureus*, including Newman, Cowan etc. Protein A may also be purchased from commercial purveyors, such as, e.g., Sigma, Repligen and GE. Methods to isolate Protein A from a natural source have been described, for example, in the following references: "Nucleotide sequence analysis of the gene for protein A from *Staphylococcus aureus* Cowan 1 (NCTC8530) and its enhanced expression in *Escherichia coli.* "Shuttleworth H. L., Duggleby C. J., Jones S. A., Atkinson T., Minton N. P. Gene 58:283-295(1987); "Structural studies on the four repetitive Fc-binding regions in protein A from *Staphylococcus aureus*." Sjoedahl J. Eur. J. Biochem. 78:471-490 (1977); These isolated Protein As may be used to form the crystals and methods described herein.

Alternatively, recombinant Protein A may be used to form the crystals and methods provided herein. In some instances, recombinant Protein A encompass or are encoded by sequences from a naturally occurring Protein A sequence. Further, Protein A comprising an amino acid sequence that is homologous or substantially identical to a naturally occurring sequence are herein described. Also, Protein A encoded by a nucleic acid that is homologous or substantially identical to a naturally occurring Protein A-encoding nucleic acid are provided and may be crystallized and/or administered as described herein.

Polypeptides referred to herein as "recombinant" are polypeptides which have been produced by recombinant DNA methodology, including those that are generated by procedures which rely upon a method of artificial recombination, such as the polymerase chain reaction (PCR) and/or cloning into a vector using restriction enzymes. "Recombinant" polypeptides are also polypeptides having altered expression, such as a naturally occurring polypeptide with recombinantly modified expression in a cell, such as a host cell.

In one embodiment, Protein A is recombinantly produced from a nucleic acid that is homologous to a *Staphylococcus aureus* Protein A nucleic acid sequence, and sometimes it is modified, e.g., to increase or optimize recombinant production in a heterologous host.

Protein A polypeptides useful for forming Protein A crystals may be expressed in a host cell, such as a host cell comprising a nucleic acid construct that includes a coding sequence for an Protein A polypeptide or a functional fragment thereof. A suitable host cell for expression of Protein A may be yeast, bacteria, fungus, insect, plant, or mammalian cell, for example, or transgenic plants, transgenic animals or a cell-free system. Preferably, a host cell is capable of glycosylating the Protein A polypeptide if necessary, capable of disulfide linkages, capable of secreting the Protein A, and/or capable of supporting multimerization of Protein A polypeptides. Preferred host cells include, but are not limited to *E. coli* (including *E. coli* Origami B and *E. coli* BL21), *Pichia pastoris, Saccharomyces cerevisiae, Schizosaccharomyces pombe, Bacillus subtilis, Aspergillus*, Sf9 cells, Chinese hamster ovary (CHO), 293 cells (human embryonic kidney), and other human cells. Also transgenic plants, transgenic animals including pig, cow, goat, horse, chicken, and rabbit are suitable hosts for production of Protein A.

For recombinant production of Protein A, a host or host cell should comprise a construct in the form of a plasmid, vector, phagemid, or transcription or expression cassette that comprises at least one nucleic acid encoding an Protein A or a functional fragment thereof. A variety of constructs are available, including constructs which are maintained in single copy or multiple copy, or which become integrated into the host cell chromosome. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.); Novagen (Madison, Wis.); Stratagene (La Jolla, Calif.); and Deutsche Sammlung von Mikroorganismen und Zellkulturen GmbH (DSMZ), (Braunschweig, Germany).

Recombinant expression of Protein A is optionally controlled by a heterologous promoter, including a constitutive and/or inducible promoter. Promoters such as, e.g., T7, the alcohol oxidase (AOX) promoter, the dihydroxy-acetone synthase (DAS) promoters, the Gal 1,10 promoter, the phosphoglycerate kinase promoter, the glyceraldehyde-3-phosphate dehydrogenase promoter, alcohol dehydrogenase promoter, copper metallothionein (CUP1) promoter, acid phosphatase promoter, CMV and promoters polyhedrin are also appropriate. The particular promoter is selected based on the host or host cell. In addition, promoters that are inducible by methanol, copper sulfate, galactose, by low phosphate, by alcohol, e.g., ethanol, for example, may also be used and are well known in the art.

A nucleic acid that encodes Protein A may optionally comprise heterologous sequences. For example, a secretion sequence is included at the N-terminus of an Protein A polypeptide in some embodiments. Signal sequences such as those from a Mating Factor, BGL2, yeast acid phosphatase (PHO), xylanase, alpha amylase, from other yeast secreted proteins, and secretion signal peptides derived from other species that are capable of directing secretion from the host cell may be useful. Similarly other heterologous sequences such as linkers (e.g., comprising a cleavage or restriction endonuclease site) and one or more expression control elements, an enhancer, a terminator, a leader sequence, and one or more translation signals are within the scope of this description. These sequences may optionally be included in a construct and/or linked to the nucleic acid that encodes Protein A. Unless otherwise specified, "linked" sequences can be directly or indirectly associated with one another.

Similarly, an epitope or affinity tag such as Histidine, HA (hemagglutinin peptide), maltose binding protein, AviTag®, FLAG, or glutathione-S-transferase may be optionally linked to the Protein A polypeptide. A tag may be optionally cleavable from the Protein A after it is produced or purified. A skilled artisan can readily select appropriate heterologous sequences, for example, match host cell, construct, promoter, and/or secretion signal sequence.

Protein A homologs or variants differ from an Protein A reference sequence by one or more residues. Structurally similar amino acids can be substituted for some of the specified amino acids, for example. Structurally similar amino acids include: (I, L and V); (F and Y); (K and R); (Q and N); (D and E); and (G and A). Deletion, addition, or substitution of amino acids is also encompassed by the Protein A homologs described herein. Such homologs and variants include (i) polymorphic variants and natural or artificial mutants, (ii) modified polypeptides in which one or more residues is modified, and (iii) mutants comprising one or more modified residues.

A Protein A polypeptide or nucleic acid is "homologous" (or is a "homolog") if it is at least about 40%, 50%, 60%, 70%, 75%, 80%, 85%, 90%, 95%, 97%, 98%, 99%, or 100% identical to a reference sequence. If the homolog is not identical to the reference sequence, it is a "variant." A homolog is "substantially identical" to a reference Protein A sequence if the nucleotide or amino acid sequence of the homolog differs from the reference sequence (e.g., by truncation, deletion, substitution, or addition) by no more than about 1, 2, 3, 4, 5, 8, 10, 20, 50 or more residues, and retains (or encodes a polypeptide that retains) the ability to bind to immunoglobulins/antibodies or its Fab fragments. Fragments of a Protein A may be homologs, including variants and/or substantially identical sequences. By way of example, homologs may be derived from various sources of Protein A, or they may be derived from or related to a reference sequence by truncation, deletion, substitution, or addition mutation. Percent identity between two nucleotide or amino acid sequences may be determined by standard alignment algorithms such as, for example, Basic Local Alignment Tool (BLAST) described in Altschul et al., *J. Mol. Biol.*, 215:403 410 (1990), the algorithm of Needleman et al., *J. Mol. Biol.*, 48:444 453 (1970), or the algorithm of Meyers el al., *Comput. Appl. Biosci.* 4:11 17 (1988). Such algorithms are incorporated into the BLASTN, BLASTP, and "BLAST 2 Sequences" programs (reviewed in McGinnis and Madden, *Nucleic Acids Res.* 32:W20-W25, 2004). When utilizing such programs, the default parameters can be used. For example, for nucleotide sequences the following settings can be used for "BLAST 2 Sequences": program BLASTN, reward for match 2, penalty for mismatch 2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON. The amino acid and nucleic acid sequences for Protein A that are appropriate to form the crystals described herein, may include homologous, variant, or substantially identical sequences.

Preparation of Cross-Linked Protein Crystals—Protein Crystallization

Protein crystals are grown by controlled crystallization of protein out of aqueous solution or aqueous solution-containing organic solvents. Conditions to be controlled include, for example, the rate of evaporation of solvent, the presence of appropriate co-solutes and buffers, pH and temperature. A comprehensive review of the various factors affecting the crystallization of proteins has been published by McPherson, Methods Enzymol., 114, pp. 112-20 (1985). McPherson and Gilliland, J. Crystal Growth, 90, pp. 51-59 (1988) have compiled comprehensive lists of proteins and nucleic acids that have been crystallized, as well as the conditions under which they were crystallized. A compendium of crystals and crystallization recipes, as well as a repository of coordinates of solved protein and nucleic acid structures, is maintained by the Protein Data Bank at the Brookhaven National Laboratory [world wide web site: pdb.bnl.gov; Bernstein et al., J. Mol. Biol., 112, pp. 535-42 (1977)]. These references can be used to determine the conditions necessary for crystallization of a protein, as a prelude to the formation of an appropriate cross-linked protein crystal, and can guide the crystallization strategy for other proteins. Alternatively, an intelligent trial and error search strategy can, in most instances, produce suitable crystallization conditions for many proteins, provided that an acceptable level of purity can be achieved for them [see, e.g., C. W. Carter, Jr. and C. W. Carter, J. Biol. Chem., 254, pp. 12219-23 (1979)].

The large single crystals which are needed for X-ray diffraction analysis are not required for use in the methods described herein. Microcrystalline showers are suitable.

For example, the cross-linked protein crystals may have a longest dimension between about 0.01 µm and about 500 µm, alternatively, between 0.1 µm and about 50 µm. They may also have a shape selected from the group consisting of: spheres, needles, rods, plates, such as hexagons and squares, rhomboids, cubes, bipyramids and prisms.

In general, crystals are produced by combining the protein to be crystallized with an appropriate aqueous solvent or aqueous solvent containing appropriate crystallization agents, such as salts or organic solvents. The solvent is combined with the protein and may be subjected to agitation at a temperature determined experimentally to be appropriate for the induction of crystallization and acceptable for the maintenance of protein activity and stability. The solvent can optionally include co-solutes, such as divalent cations, co-factors or chaotropes, as well as buffer species to control pH. The need for co-solutes and their concentrations are determined experimentally to facilitate crystallization.

In an industrial-scale process, the controlled precipitation leading to crystallization can best be carried out by the simple combination of protein, precipitant, co-solutes and, optionally, buffers in a batch process. As another option, proteins may be crystallized by using protein precipitates as the starting material. In this case, protein precipitates are added to a crystallization solution and incubated until crystals form. Alternative laboratory crystallization methods, such as dialysis or vapor diffusion, can also be adopted. McPherson, supra and Gilliland, supra, include a comprehensive list of suitable conditions in their reviews of the crystallization literature.

Occasionally, incompatibility between the crosslinking agent and the crystallization medium might require exchanging the crystals into a more suitable solvent system.

Many of the proteins for which crystallization conditions have already been described, may be used to prepare cross-linked protein crystals according to this invention. It should be noted, however, that the conditions reported in most of the above-cited references have been optimized to yield, in most instances, a few large, diffraction quality crystals. Accordingly, it will be appreciated by those of skill in the art that some degree of adjustment of these conditions to provide a high yielding process for the large scale production of the smaller crystals used in making cross-linked protein crystals may be necessary.

Preparation of Cross-Linked Protein Crystals—Crosslinking of Protein Crystals

Stabilized Crystals. Once Protein A crystals have been grown in a suitable medium they can be optionally stabilized, such as by cross-linking. Cross-linking results in stabilization of the crystal lattice by introducing covalent links between the constituent protein molecules of the crystal. This makes possible transfer of the protein into an alternate environment that might otherwise be incompatible with the existence of the crystal lattice or even with the existence of intact protein. Protein A crystals may be cross-linked through, e.g., lysine amine groups, thiol (sulfhydryl) groups, and carbohydrate moieties. Cross-linked crystals are also referred to herein as "Protein A-CLPC," "CLPC-Protein A," or "CLPC."

A cross-linked crystal may alter the stability (e.g., pH, temperature, mechanical and/or chemical stability), the pH profile of antibody binding, the solubility, the uniformity of crystal size or volume, the rate of release of bound antibody from the crystal, and/or the pore size and shape between individual molecules in the underlying crystal lattice.

Advantageously, cross-linking or stabilizing according to the present invention is carried out in such a way that the crystals comprise a Protein A that shows at least about 60%, 80%, 100%, 150%, 200%, 250%, 300% or more of the binding capacity/per mL of crystals (binding of antibodies) as compared to immobilized Protein A per mL of the gel. Stability may be increased by at least about 30%, 40%, 50%, 60%, 70%, 80%, 90%, 100%, 150%, 200%, 250%, 300% or more as compared to soluble or immobilized Protein A. Stability can be measured under conditions of storage, such as pH stability, temperature stability, stability against proteases, dissolution stability, and as in vitro column stability, for example.

In some embodiments, cross-linking slows the dissolution of the Protein A polypeptides in the crystal into solution, effectively immobilizing the protein molecules into microcrystalline particles. Upon exposure to a trigger in the environment surrounding the cross-linked protein crystals, such as under conditions of use rather than storage, the protein molecules slowly dissolve, releasing active Protein A polypeptide and/or increasing Protein A activity. The rate of dissolution is controlled, for example, by one or more of the following factors: the degree of cross-linking, the length of time of exposure of protein crystals to the cross-linking agent, the rate of addition of cross-linking agent to the protein crystals, the nature of the cross-linker, the chain length of the cross-linker, pH, temperature, presence of sulfahydryl reagents like cysteine, glutathione, the surface area of the cross-linked protein crystals, the size of the cross-linked protein crystals, and the shape of the cross-linked protein crystals.

Cross-linking can be achieved using one or a combination of a wide variety or cross-linking agents, including a multifunctional agent, at the same time (in parallel) or in sequence. Upon exposure to a trigger in the surrounding environment, or over a given period of time, the cross-links between protein crystals cross-linked with such multifunctional cross-linking agents lessen or weaken, leading to protein dissolution or release of activity. Alternatively, the cross-links may break at the point of attachment, leading to protein dissolution or release of activity. See U.S. Pat. Nos. 5,976,529 and 6,140,475.

In some embodiments, the cross-linking agent is a multifunctional cross-linking agent having at least 2, 3, 4, 5, or more active moieties. In various embodiments, the agent may be chosen from glutaraldehyde, succinaldehyde, octanedialdehyde, glyoxal, dithiobis(succinimidylpropionate), 3,3' dithiobis(sulfosuccinimidylpropionate), dimethyl 3,3'-dithiobispropionimidate-HCl. N-succinimidyl-3-(2-pyridyldithio)propionate, hexamethylenediamine, diaminooctane, ethylenediamine, succinic anhydride, phenylglutaric anhydride, salicylaldchyde, acctimidate, formalin, acrolein, succinic scmialdchyde, butyraldehyde, dodecylaldehyde, glyceraldehyde, and trans-oct-2-enal.

Additional multifunctional cross-linking agents include halo triazines, e.g., cyanuric chloride; halo-pyrimidines, e.g., 2,4,6-trichloro/bromo pyrimidine; anhydrides or halides of aliphatic or aromatic mono- or di-carboxylic acids, e.g., maleic anhydride, (meth)acryloyl chloride, chloroacetyl chloride; N-methylol compounds, e.g., N-methylol chloroacetamide; di-isocyanates or di-isothiocyanates, e.g., phenylene-1,4-di-isocyanate and aziridines. Other cross-linking agents include epoxides, such as, for example, di-epoxides, tri-epoxides and tetra-epoxides. In one embodiment, the cross-linking agent is glutaraldehyde, a bifunctional agent, and glutaraldehyde is used alone or in sequence with an epoxide. Other cross-linking reagents (see, for example, the 1996 catalog of the Pierce Chemical Company) may also be used, at the same time (in parallel) or in sequence with reversible cross-linking agents, such as those described below.

According to an alternate embodiment of this invention, cross-linking may be carried out using reversible cross-linking agents, in parallel or in sequence. The resulting cross-linked protein crystals are characterized by a reactive multifunctional linker, into which a trigger is incorporated as a separate group. The reactive functionality is involved in linking together reactive amino acid side chains in a protein and the trigger consists of a bond that can be broken by altering one or more conditions in the surrounding environment (e.g., pH, presence of reducing agent, temperature, or thermodynamic water activity).

The cross-linking agent may be homofunctional or heterofunctional. The reactive functionality (or moiety) may, e.g., be chosen from one of the following functional groups (where R, R', R", and R'" may be alkyl, aryl or hydrogen groups):

I. Reactive acyl donors, such as, e.g.: carboxylate esters RCOOR', amides RCONHR', Acyl azides $RCON_3$, carbodiimides R—N=C=N—R', N hydroxyimide esters, RCO—O—NR', imidoesters R—C=$NH2^+$(OR'), anhydrides RCO—O—COR', carbonates RO—CO—O—R', urethanes RNHCONHR', acid halides RCOHal (where Hal=a halogen), acyl hydrazides RCONNR'R", and O acylisoureas RCO—O—C=NR'(—NR"R'")

II. Reactive carbonyl groups, such as, e.g.: aldehydes RCHO and ketones RCOR', acetals $RCO(H_2)R'$, and ketals RR'CO2R'R" (Reactive carbonyl containing functional groups known to those well skilled in the art of protein immobilization and cross-linking are described in the literature (Pierce Catalog and Handbook, Pierce Chemical Company, Rockford, Ill. (1994); S. S. Wong, Chemistry of Protein Conjugation and Cross-linking. CRC Press, Boca Raton, Fla. (1991));

III. Alkyl or aryl donors, such as, e.g.: alkyl or aryl halides R-Hal, azides R—$N_3$, sulfate esters $RSO_3R'$, phosphate esters $RPO(OR'_3)$, alkyloxonium salts $R_3O+$, sulfonium $R_3S+$, nitrate esters $RONO_2$, Michael acceptors RCR'=CR'"COR", aryl fluorides ArF, isonitriles RN+=C—, haloamines $R_2N$-Hal, alkenes, and alkynes;

IV. Sulfur containing groups, such as, e.g.: disulfides RSSR', sulfhydryls RSH, and epoxides $R_2C\_^°CR'_2$; and V. Salts, such as, e.g.: alkyl or aryl ammonium salts $R_4N+$, carboxylate RCOO—, sulfate $ROSO_3$—, phosphate $ROPO_3$", and amines $R_3N$.

Reversible cross-linking agents, for example, comprise a trigger. A trigger includes an alkyl, aryl, or other chain with an activating group that can react with the protein to be cross-linked. Those reactive groups can be any variety of groups such as those susceptible to nucleophilic, free radical or electrophilic displacement including halides, aldehydes, carbonates, urethanes, xanthanes, and epoxides among others. For example, reactive groups may be labile to acid, base, fluoride, enzyme, reduction, oxidation, thiol, metal, photolysis, radical, or heat.

Additional examples of reversible cross-linking agents are described in T. W. Green, Protective Groups in Organic Synthesis, John Wiley & Sons (Eds.) (1981). Any variety of strategies used for reversible protecting groups can be incorporated into a cross-linker suitable for producing cross-linked protein crystals capable of reversible, controlled solubilization. Various approaches are listed, in Waldmann's review of this subject, in *Angewante Chemie Inl. Ed. Engl.*, 35:2056 (1996).

Other types of reversible cross-linking agents are disulfide bond-containing cross-linkers. The trigger breaking cross-links formed by such cross-linking agents is the addition of reducing agent, such as cysteine, to the environment of the cross-linked protein crystals. Exemplary disulfide cross-linking agents are described in the Pierce Catalog and Handbook (1994-1995). Examples of such cross-linkers and methods are disclosed in U.S. Pat. No. 6,541,606, relevant portions of which are incorporated herein by reference.

In addition, cross-linking agents which cross-link between carbohydrate moieties or between a carbohydrate moiety and an amino acid may also be used.

The concentration of the cross-linking agent may be from about 0.01% to 20%, about 0.02% to 10%, or about 0.05% to 5% w/v in solution. Typically, the crosslinking agent is about 0.5% or about 1% w/v. For example, the concentration of the cross-linking agent may be, e.g., about 0.01%, 0.02%, 0.05%, 0.075%, 0.1%, 0.2%, 0.3%, 0.5%, 1%, 2%, 3%, 3.5%, 4%, 5%, 6%, 7%, 8%, 9%, 10%, 15%, or 20% w/v in solution. It may be necessary to exchange buffers prior to cross-linking. Crystals, including CLPCs, may be optionally lyophilized or otherwise formulated.

The crystals, including the cross-linked crystals described herein are useful in the methods of treatment and methods to reduce IgG levels of circulating immune complexes such as in immune thrombocytopenic purpura. The Protein A crystals are also useful in methods relating to purification processes (e.g., monoclonal antibody purification, polyclonal antibody purification, purification of immunoglobulins, IgGs and its subtypes, Fab fragments, single chain antibodies etc. from various sources either in column format or impregnated in a membrane or in polymers or coating or immobilized on a support. The crystals described herein can be applied to these uses, based on one or more properties of the stabilized Protein A crystals described above.

Drying of Crystals/CLPCs of Protein A. Crystals of Protein A are dried by removal of water, organic solvent or liquid polymer by drying means including drying with $N_2$, air or inert gases, vacuum oven drying, lyophilization, washing with a volatile organic solvent followed by evaporation of the solvent, evaporation in a fume hood, tray drying, fluid-bed drying, spray drying, vacuum drying, or roller drying. Typically, drying is achieved when the crystals become a free-flowing powder. Drying may be carried out by passing a stream of gas over wet crystals. The gas may be selected from the group consisting of: nitrogen, argon, helium, carbon dioxide, air or combinations thereof.

In principle, dried crystals can be prepared by lyophilization. However, this technique involves rapid cooling of the material and can be applied only to freeze stable products. In one embodiment, the aqueous solution containing a crystalline/CLPC Protein A is first frozen to between −40 and −50° C., followed by removal of the under vacuum.

Production of crystals of Protein a/CLPC, or formulations or compositions comprising such crystals. In one aspect, crystals of Protein A/CLPC, or formulations or compositions comprising such crystals are disclosed. Such compositions can be prepared according to the following process:

First, the Protein A is crystallized. Next, excipients or ingredients selected from sugars, sugar alcohols, viscosity increasing agents, wetting or solubilizing agents, buffer salts, emulsifying agents, antimicrobial agents, antioxidants, and coating agents are added directly to the mother liquor. Alternatively, the mother liquor is removed, after which the crystals are suspended in an excipient solution for a minimum of 1 hour to a maximum of 24 hours. The excipient concentration is typically between about 0.01 and about 10% (w/w). The ingredient concentration is between about 0.01 and about 90% (w/w). The crystal concentration is between about 0.01 and about 99% (w/w).

The mother liquor is then removed from the crystal slurry either by filtration or by centrifugation. Subsequently, the crystals are washed optionally with solutions of about 50 to 100% (w/w) of one or more organic solvents such as, for example, ethanol, methanol, isopropanol or ethyl acetate, either at room temperature or at temperatures between about −20° C. to about 25° C.

The crystals are then dried either by passing a stream of nitrogen, air, or inert gas over them. Alternatively, the crystals are dried by air drying, spray drying, lyophilization or vacuum drying. The drying is carried out for a minimum of about 1 hour to a maximum of about 72 hours after washing, until the moisture content of the final product is below about 10% by weight, most preferably below about 5% by weight. Finally, micromizing (reducing the size) of the crystals can be performed if necessary.

According to one embodiment of this invention, when preparing crystals of Protein A/CLPC, or formulations or compositions comprising such crystals, enhancers, such as surfactants, are not added during crystallization. Excipients or ingredients are added to the mother liquor after crystallization, at a concentration of between about 1 and about 10% (w/w), alternatively at a concentration of between about 0.1 and about 25% (w/w), alternatively at a concentration of between about 0.1 and about 50% (w/w). The excipient or ingredient is incubated with the crystals in the mother liquor for about 0.1 to about 3 hrs, alternatively the incubation is carried out for about 0.1 to about 12 hrs, alternatively the incubation is carried out for about 0.1 to about 24 hrs.

In another embodiment of this invention, the ingredient or excipient is dissolved in a solution other than the mother liquor, and the crystals are removed from the mother liquor and suspended in the excipient or ingredient solution. The ingredient or excipient concentrations and the incubation times are the same as those described above.

Another advantage of the present invention is that crystals of Protein A/CLPC, or formulations thereof that are encapsulated within polymeric carriers to form compositions comprising microspheres can be dried by lyophilization. Lyophilization, or freeze-drying allows water to be separated from the composition. The Protein A/CLPC crystal composition is first frozen and then placed in a high vacuum. In a vacuum, the crystalline water sublimes, leaving the Protein A/CLPC crystal composition behind, containing only the tightly bound water. Such processing further stabilizes the composition and allows for easier storage and transportation at typically encountered ambient temperatures.

Spray drying allows water to be separated from the crystal preparation. It is highly suited for the continuous production of dry solids in either powder, granulate or agglomerate form from liquid feedstocks as solutions, emulsions, and pumpable suspensions. Spray drying involves the atomization of a liquid feedstock into a spray of droplets and contacting the droplets with hot air in a drying chamber. The sprays are produced by either rotary (wheel) or nozzle atomizers. Evaporation of moisture from the droplets and formation of dry particles proceed under controlled temperature and airflow conditions. Relatively high temperatures are needed for spray drying operations. However, heat damage to products is generally only slight, because of an evaporative cooling effect during the critical drying period and because the subsequent time of exposure to high temperatures of the dry material may be very short. Powder is discharged continuously from the drying chamber. Operating conditions and dryer design are selected according to the drying characteristics of the product and the powder specification. Spray drying is an ideal process where the end product must comply with precise quality standards regarding particle size distribution, residual moisture content, bulk density and particle shape.

Protein A-CLPC useful in the methods of this invention may be combined with an excipient. According to this invention, an "excipient" acts as a filler or a combination of fillers used in pharmaceutical compositions. Examples of excipients are described in Handbook of Pharmaceutical Excipients, published jointly by the American Pharmaceutical Association and the Pharmaceutical Society of Great Britain, and further examples are set forth below. Preferred excipients included in this category are: Salts of either 1) amino acids such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trchalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. A further preferred group of excipients includes sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin, polylysine, polyarginine.

In one embodiment of this invention, the excipient is selected from the group consisting of: salts, alcohols, carbohydrates, proteins, lipids, surfactants, polymers and polyamino acids. In another embodiment, the excipient is selected from the group consisting of: Protamine, polyvinylalcohol, cyclodextrins, dextrans, polyamino acids, such as polyarginine, polylysine and poly glutamate, polyethylene glycol and dendrimers, polymers such polycarbophil, alginate.

Compositions. Protein A crystals, including cross-linked crystals are provided as a composition, such as a pharmaceutical composition (see, e.g., U.S. Pat. No. 6,541,606, describing formulations and compositions of protein crystals). Pharmaceutical compositions comprising Protein A crystals include the Protein A crystal with one or more ingredients or excipients, including, but not limited to sugars and biocompatible polymers.

The Protein A-CLPC may be administered as a crystal in a composition as any of a variety of physiologically acceptable salt forms, and/or with an acceptable pharmaceutical carrier and/or additive as part of a pharmaceutical composition. Physiologically acceptable salt forms and standard pharmaceutical formulation techniques and excipients are well known to persons skilled in the art (see, e.g., Physician's Desk Reference (PDR) 2003, 57th ed., Medical Economics Company, 2002; and Remington: The Science and Practice of Pharmacy, eds. Gennado et al., 20th ed, Lippincott, Williams & Wilkins, 2000). For the purposes of this application, "formulations" include "crystal formulations." Other useful ingredients and excipients for the Protein A crystal compositions include the following:

Biocompatible Polymers. Biocompatible polymers are polymers that are non-antigenic (when not used as an adjuvant), non-carcinogenic, non-toxic and which are not otherwise inherently incompatible with living organisms may be used in the Protein A crystal compositions described herein. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutryate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Biodegradable Polymers, i.e., polymers that degrade by hydrolysis or solubilization may be included in Protein A crystal compositions. Degradation can be heterogenous (occurring primarily at the particle surface), or homogenous (degrading evenly throughout the polymer matrix).

Ingredients such as one or more excipients or pharmaceutical ingredients or excipients may be included in Protein A crystal compositions. An ingredient may be an inert or active ingredient.

The present invention is applicable to IgG's in general, regardless of source. Preferred IgG's for the purposes of this invention are human and mouse IgG classes. The proteins from which the species of interest may be separated are other immunoglobulins, such as, for example, IgM and IgE, and other proteins such as, for example, albumins. The binding affinity of these proteins for protein A is known to be much less than that of IgG's.

Any inorganic salt which is soluble in an aqueous medium may be used. Examples include alkali and alkaline earth metal halides and sulfates. Positively charged ions such as ammonium may be substituted for the metallic ions. The salt must also be nonreactive toward the immunoglobulins, the protein A or any support to which the protein A is bound. The salt concentration may range from about 0.5 M up to the solubility limit, preferably from about 1.0 M to about 4.0 M. The exact pH of the solution is not critical and can vary widely within the range from approximately neutral to mildly alkaline. Thus, the pH may be greater than or equal to approximately 7.0, preferably from about 8.5 to about 9.5.

The salt is preferably used as part of a buffer solution, the buffering effect created by either the salt itself or by a separate component in the mixture. Conventional buffers can be used, appropriately selected to achieve the desired pH.

For immobilization purposes, the protein A is crystallized and cross-linked without any solid support, such as the packing material in an affinity chromatography column.

When the present invention is used to enhance separation in affinity chromatography, it is preferable to equilibrate the column packing by repeated washings with a buffer solution containing a high salt concentration, and also to dilute the sample mixture in the same buffer solution before adding it to the column. The dilution may also vary widely, although dilutions ranging from about 1:1 to about 1:20 are preferred. As the buffer solution passes through the column, non-binding proteins will be carried with the buffer solution which thereby separates them from the bound immunoglobulins. The recovery of the immunoglobulins is then achieved by elution with an acidic buffer, preferably having a pH ranging from about 2.0 to about 5.0, more preferably from about 2.5 to about 4.0.

The nature of the column is not critical and can vary widely, ranging from an open column to a pressurized column. The strong binding inherent in the invention permits an effective separation to be achieved by the use of an open column.

A "sample containing a target protein" as used in this specification refers to any sample containing the target protein, whether naturally derived or artificially prepared. The sample can include mixtures of different liquids, a liquid and a solid, or different solids. Examples of a sample containing a target protein can include blood, serum, ascites fluid, milk, a tissue sample, a cell culture, a cell lysate, or the supernatant of a cell culture.

"Support" as used in this specification refers to anything to which a Protein A can be immobilized to obtain an affinity chromatography medium, regardless of its form or the material from which it is made. Examples include agarose, which is often used in affinity chromatography, cellulose; and polyacrylamide.

"Chromatography medium" as used in this specification refers to a stationary phase used for chromatographic purification regardless of its configuration (column or planar), state (liquid or solid), or the material from which it is made. Common examples of chromatography media used for protein purification include an ion exchange resin, an affinity stationary phase, and a gel permeation stationary phase.

"Coupled" as used in this specification refers to the direct contact as well as the disposition of a linker gene or protein between two or more types of genes or proteins. It also includes the coupling through covalent or non-covalent bonds.

"Target protein" as used in this specification refers to any protein to be purified. An example of a target protein can be an antibody.

A "fusion protein" refers herein to any combination of two or more separate polypeptides. The fusion protein includes a combination of two or more separate polypeptides wherein the two or more polypeptides are covalently linked. The fusion protein includes a combination of two or more separate polypeptides wherein the two or more separate polypeptides are non-covalently linked. The two or more separate polypeptides may directly contact with each other without any mediator. The two or more separate polypeptides may be mediated by a mediator such as a linker peptide.

The method disclosed herein uses the high binding specificity between a Protein A and a target protein such as antibody.

In an embodiment, the method includes contacting a sample containing a target protein to a support having immobilized thereon a crystalline cross-linked Protein A, wherein the target protein is a antibody and the Protein A-CLPC has specific binding affinity for the antibody, and wherein the contact is under conditions such that the Protein A binds to the antibody; removing components of the sample that are not bound; and then removing the target protein/antibody from the support. In some embodiments, the sample is a cell lysate, a cell culture, the supernatant of a cell culture, or a biological fluid containing the target protein. In some embodiments, the support having immobilized thereon a cross-linked Protein A is configured as an affinity chromatography column.

In the method and column for the purification of proteins disclosed herein, a disposable column may be used. The disposable column may have a diameter of about 0.1 to about 1.0 mm, about 0.3 to about 0.7 mm, or about 0.5 mm. The column may be placed in a glass test tube of about 16×125 mm. In an embodiment, a disposable column having the diameter of 0.5 mm is placed in a 16×125 mm glass test tube. The chromatography medium, e.g., Protein A-CLPC, may be packed into the column according to any method known in the art. In an embodiment using a disposable column, a sufficient volume of degassed buffer/water is added to the column to fill it up to the reservoir (wide-mouth) portion, then any air bubbles are eliminated from the column. After that, the gel (Protein A-CLPC) can be packed into the column with degassed 50% gel slurry, and degassed buffer solution (or water) at room temperature. Sufficient volume of degassed gel slurry can be added to obtain the desired settled gel volume. The gel can be permitted to settle down in the column for at least 30 minutes. The packed column can be stored and used at 4° C.

Removing the target protein from the support can comprise eluting the target protein from the support. Eluting the target protein can be conducted by elution at a pH that lowers the binding affinity between the Protein A-CLPC and the antibody such that the target protein/antibody is removed from the support (Protein A-CLPC).

The first step in the process of the present invention requires a buffer having a pH in the range of about pH 7.0 to pH 10 and a combination of monovalent cations and polybasic anions in a concentration of about 0.01M to 2M. Any buffer may be used to provide the desired pH. For example phosphate buffer, glycine buffer, borate buffer or tris buffer can be used. The concentration of buffer should be in the range of about 0.01M to 0.25M. In addition, salts of NaCl, KCl, tetramethylammonium chloride (TMAC), tetraethylammonium chloride (TEAC), tetrapropylammonium chloride and tetrabutylammonium chloride etc can be added to the buffer in the concentration range of about 0.05M to 2.0M.

Where the monovalent cations are potassium ions or sodium ions and the polybasic anions are phosphate ions the potassium ions and phosphate ions can be provided by the use of potassium phosphate either in the form of tripotassium phosphate, $K_3PO_4$, dipotassium hydrogen phosphate, $K_2HPO_4$ or monopotassium dihydrogen phosphate, $KH_2PO_4$, since the pH of the medium controls the proportion of the various phosphate ions which are present. The potassium ions and phosphate ions should be present in a concentration in the range of about 0.6M to 1.75M. A concentration of about 1.0M to 1.5M has been found especially satisfactory.

Other combinations of monovalent cations and polybasic anions which have adequate solubilities at the high concentrations used in the present invention, include ammonium phosphates in concentrations of about 1.0M to 1.5M, ammonium sulfates in concentrations of about 1.0M to 1.5M and sodium sulfates in concentrations of about 1.0M to 1.25M. Other combinations may be used as well so long as the salts do not precipitate at the concentrations used.

As pointed out above, the adsorbent (Protein A-CLEC) is preferably used in a column to facilitate contact with the immunoglobulins to be purified. Prior to application of the medium containing the impure immunoglobulins to the column, the column containing Protein A-CLEC is equilibrated with several bed volumes of buffer containing the combination of to the column, the column is equilibrated with several bed volumes of buffer containing the combination of monovalent cations and polybasic anions at concentrations in the range of about 0.01M to 4M. This ensures that the environment is optimum for binding the immunoglobulins to the column. The medium containing the immunoglobulins to be purified, such as an immune serum or other source of immunoglobulins is mixed with the buffer containing the combination of monovalent cations and polybasic anions. The resulting mixture is then applied to the column, resulting in adsorption of the immunoglobulins to the column. The column is then washed with additional buffer containing the combination of monovalent cations and polybasic anions in order to elute from the column impurities which are not strongly adsorbed to the column. The immunoglobulins on the other hand are strongly adsorbed to the column because of the enhanced affinity of the adsorbent for the immunoglobulins as a result of the presence of the buffer containing the combination of monovalent cations and polybasic anions. Following removal of the undesired impurities by washing with the same buffer solution, the purified immunoglobulins are eluted from the column by means of a buffer having an acidic pH, namely a pH in the range of about pH 2.0 to pH 6.0. At pH 6.0 a part of the immunoglobulins, principally the $IgG_1$ fraction, is eluted. As the pH is lowered the remainder of the immunoglobulins, including the $IgG_{2a}$ and $IgG_{2b}$, fractions, is eluted. The immunoglobulins can be eluted using a pH 2.0 buffer, which is effective to elute all of the immunoglobulins. However, if desired, a fraction of the immunoglobulins can be eluted at pH 6.0. Various other fractions can be eluted, if so desired, by lowering the pH between pH 6.0 and pH 2.0. By lowering the pH in steps, it is possible to isolate purified fractions of immunoglobulins which contain specific immunoglobulins as desired. Any buffer can be used for elution. For example an acetic acid-acetate buffer or glycine. HCl buffer can be used for this purpose. A buffer concentration in the range of about 0.01M to 0.25M can be used. A buffer concentration of about 0.1M to 0.2M is especially preferred.

The immunoglobulins or fractions thereof can be bound to a short column of Protein A-CLEC when compared to immobilized Protein A bound to support such as agarose for example. The isolated immunoglobulins or fractions thereof can be recovered in yields which are as much as ninety percent (90%). Even binding obtained using the most sophisticated techniques previously available can be improved by as much as 2 to 10%.

In certain embodiments, the primary recovery sample is subjected to affinity chromatography to further purify the antibody of interest away from HCPs. In certain embodiments the chromatographic material is capable of selectively or specifically binding to the antibody of interest. Non-limiting examples of such chromatographic material include: Protein A, Protein G, Protein L. In specific embodiments, the affinity chromatography step involves subjecting the primary recovery sample to a column comprising a suitable Protein A resin. Protein A resin is useful for affinity purification and isolation of a variety antibody isotypes, particularly $IgG_1$, $IgG_2$, and $IgG_4$.

A non-limiting example of a suitable column packed with Protein A-CLPC is about 1.0 cm diameter×about 21.6 cm long column (17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a Protein A-CLPC.

In certain embodiments it will be advantageous to identify the dynamic binding capacity (DBC) of the Protein A resin in order to tailor the purification to the particular antibody of interest. For example, but not by way of limitation, the DBC of a Protein A-CLPC column can be determined either by a single flow rate load or dual-flow load strategy. The single flow rate load can be evaluated at a velocity of about 300 cm/hr throughout the entire loading period. The dual-flow rate load strategy can be determined by loading the column up to about 35 mg protein/mL resin at a linear velocity of about 300 cm/hr, then reducing the linear velocity by half to allow longer residence time for the last portion of the load.

In certain embodiments, the Protein A column can be equilibrated with a suitable buffer prior to sample loading. A non-limiting example of a suitable buffer is a PBS or Tris/NaCl buffer, pH of about 7.2-7.4. A non-limiting example of suitable equilibration conditions is PBS buffer pH 7.4 or 25 mM Tris, 100 mM NaCl, pH of about 7.2. Following this equilibration, the sample can be loaded onto the column. Following the loading of the column, the column can be washed one or multiple times using, e.g., the equilibrating buffer. Other washes, including washes employing different buffers, can be employed prior to eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. A non-limiting example of a suitable elution buffer is an acetic acid/NaCl buffer, pH of about 3.5. Suitable conditions are, e.g., 0.1 M acetic acid, pH of about 3.5 or 0.2M glycine.HCl buffer, pH 2.0. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

The present invention provides protein impregnated materials suitable for use in a variety of applications including, for example, the removal of immune globulins from blood, plasma, serum, cell culture during purification or immunoprecipitation and methods of producing and using same. Such protein impregnated membranes can also be used in therapeutic, diagnostic and other industrial applications.

In an embodiment, the present invention includes membranes impregnated with a cross-linked protein crystal. The cross-linked proteins can include any suitable cross-linked protein made from a variety of suitable proteins. In an embodiment, the cross-linked proteins can include proteins capable of removing antibodies or the like from serum, plasma, blood, cell culture, such as, Protein A, Protein G, Protein L, like proteins or combinations thereof. Preferably, the cross-linked protein crystal is a Protein A-CLPC as described herein.

In an embodiment, the present invention includes a polymeric membrane, impregnated with the cross-linked protein crystals, preferably Protein A-CLPC, alone or in combination with other cross-linked protein crystals such Protein G or Protein L. It is believed that the use of Protein A-CLPC impregnated membranes will provide a number of benefits over currently available immobilization technologies including, for example: 1) Better Protein A containment without any leaching; 2) Reduced cartridge/column size resulting in enhanced ease of use; 3) Ease of use during cartridge/column manufacture; and 4) Increased safety over the existing system (due to better containment of Protein A in the cartridge).

The cross-linked protein impregnated membranes of the present invention can be made in a variety of suitable ways. In general, a polymer-based membrane casting solution is first prepared and then mixed with the desired amount and types of cross-linked protein crystals. It should be appreciated that the membrane casting solution can be made from any suitable polymer-based materials. Once formed and mixed with the cross-linked protein, the membrane casting solution is applied to a support material by, for example, spreading on the support material, and subjected to one or more precipitation and washing sequences to form a composite membrane which can be subsequently dried prior to use.

In an embodiment, the casting solution is composed of a polymeric base material, such as polyurethane or the like, in any suitable solvent including, for example, 1-methyl-2-pyrrolidinone ("NMP"), dimethylformamide ("DMF"), the like or combinations thereof. The casting solution can also include additional other components, such as a bulking agent, a hydrophilic agent (e.g., an agent that can render the membrane more hydrophilic), the like or combinations thereof. In an embodiment, the bulking agent can include zirconium oxide, zirconium phosphate, carbon, the like or combinations thereof. The bulking agent can be added in a sufficient amount to control the porosity of the membrane. The bulking agent can be added in an amount of up to about 80% of the total dry weight of the membrane, preferably about 50% of the total dry weight of the membrane. In an embodiment, the bulking agent and the cross-linked protein crystal are added in equal amounts or at least approximately equal amounts.

In an embodiment, the hydrophilic agent is polyvinylpyrrolidone ("PVP"), the like or combinations thereof. The hydrophilic agent can be added in any suitable amount to enhance the hydrophilic nature of the membrane.

The casting solution is then mixed with a suitable amount of a cross-linked Protein A. In an embodiment, the cross-linked Protein A-CLPC is added to the membrane in an amount effective to provide a desired level of binding activity. In an embodiment, the membrane is impregnated with about 3.25 mg/cm2 or less of the cross-linked protein. In this regard, the cross-linked protein crystal can amount to about 80% or less of the membrane weight.

The resultant membrane solution is then applied to a support, such as a synthetic mesh material, and immersed into water or other suitable media, such as a mixture of isopropyl alcohol and water, preferably a 50:50 ratio of isopropyl alcohol ("IPA") to water. A polymer membrane composite material can then be precipitated under suitable conditions. For example, a suitable amount of NMP can be added during water precipitation to control the rate of precipitation. In this regard, the rate of precipitation can be decreased, thus resulting in a more porous polymeric matrix of the membrane.

The Protein A-CLPC of the present invention may be administered through an extracorporeal device or catheter, such as for delivery of Protein A-CLPC to a patient. Catheters, for example, urinary catheters, may be coated with compositions containing Protein A-CLPC crystals.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Introduction

The Protein A cross-linked crystals (CLPCs) were produced so as to develop an innovative Protein A chromatography system for the purification of antibodies. Protein A CLPCs will offer the advantages of highly concentrated Protein A activity combined with high stability and chemical resistance. The condensed Protein A concentration will reduce column size, buffer volume and process time. Moreover, the cross-linking of Protein A crystals will prevent the leaching of Protein A during chromatography. Altogether, this will reduce antibody production time and cost.

The Examples herein describe the crystallization (in both hanging drops and batches) and the cross-linking of recombinant Protein A.

Purpose

To develop cross-linked Protein A crystals for antibody purification.

Equipment and Materials

Recombinant Protein A. Repligen Corporation, Cat. No. rPA50.

Recombinant Protein A. Fitzgerald International, Cat. No. 30-AP75.

Amnicon Ultra-4 centrifugal filter unit, Millipore, Cat. No. UFC801008.

Nalgene MF75 Series Disposable Sterilization Filter Units, 0.2 micron, Fisher Scientific, Cat. No. 09-740-36K.

pH conductivity meter, Denver Instrument, Model 220.

Siliconized circle cover slides: Hampton Research, Cat #HR3-233.

VDX™ plates, Hampton Research, Cat. No. HR3-140.

8453 UV-Visible Spectrophotometer, Agilent Technologies.

Ammonium sulfate, Fisher Scientific, Cat. No. BP212R-1.

Hydrochloric Acid Solution, Fisher Scientifics, Cat. No. A481-212.

Sodium cacodylate trihydrate, Sigma-Aldrich, Cat. No. C0250.

Sodium chloride, Fisher Scientific, Cat. No. S271-3.

Tris(hydroxymethyl)aminomethane (Trizma Base), Sigma-Aldrich, Cat. No. T-4661.

DI (Reverse Osmosis & De-Ionization) $H_2O$.

Crystal Screen Kit, Hampton Research, Cat. No. HR2-110.

Crystal Screen 2 Kit, Hampton Research, Cat. No. HR2-112.

JBScreen Classic 1, Jena Bioscience, Cat. No. CS-101L.

JBScreen Classic 2, Jena Bioscience, Cat. No. CS-102L.

JBScreen Classic 3, Jena Bioscience, Cat. No. CS-103L.

JBScreen Classic 4, Jena Bioscience, Cat. No. CS-104L.

Wizard I random sparse matrix crystallization screen, Emerald BioSystems.

Wizard II random sparse matrix crystallization screen, Emerald BioSystems.

Procedure

Crystallization of recombinant Protein A was carried out with the hanging-drop vapor diffusion crystallization method. The Protein A crystals were scaled up to 1 ml batch size and cross-linked.

Solution Preparation.

3.5 M Ammonium Sulfate 46.2 g of ammonium sulfate was dissolved in 100 ml DI $H_2O$, and the solution was sterile filtered.

1 M Sodium Cacodylate pH 6.5

21.4 g of sodium cacodylate was dissolved in 80 ml DI $H_2O$. The pH was adjusted to 6.5 with a concentrated HCl solution. The buffer solution was then adjusted to 100 ml with DI $H_2O$, and sterile filtered with a 0.2 micron Nalgene Filter Unit.

5 M Sodium Chloride 29.2 g of sodium chloride was dissolved in 100 ml DI $H_2O$, and the solution was sterile filtered.

In-House Formulation 4 of Wizard II Crystallization Screen

In-house formulation #4 of the Wizard II screening kit was prepared by mixing 2.86 ml of 3.5 M ammonium sulfate with 0.5 ml of 1 M sodium cacodylate pH 6.5, 0.2 ml of 5 M sodium chloride and 1.44 ml filtered DI $H_2O$.

10 mM Tris-HCl Buffer pH 7

12.11 g of Trizma Base was dissolved in 80 ml DI $H_2O$. The pH was adjusted to 7 with concentrated HCl solution. The buffer was adjusted to 100 ml with DI $H_2O$ and sterile filtered. The 1 M Tris-HCl buffer was then diluted 100 fold in filtered DI $H_2O$.

Protein A Crystallization in Hanging Drops.

The initial crystallization screening was performed with the recombinant Protein A from Fitzgerald International at 50.6 mg/ml in DI $H_2O$. Using the hanging-drop vapor diffusion crystallization method from Hampton Research (see References), the Protein A sample was screened at room temperature in 24-well plates at a 1:1 protein/reagent ratio with 8 different screening kits: JBScreen Classic 1, JBScreen Classic 2, JBScreen Classic 3, JBScreen Classic 4, Wizard I, Wizard II, Hampton Crystal Screen and Hampton Crystal Screen 2. Crystal screening was also performed with the Protein A sample that was concentrated to 120 mg/ml with an Amicon centrifugal filter unit (protein concentration was determined by spectrophotometry at 280 nm).

Protein A Crystallization in Batches.

Protein A crystallization was set up in batches with recombinant Protein A from Fitzgerald International and with one of the conditions that produced crystals in the initial hanging-drop crystallization screening (i.e. the formulation #4 of the Wizard II matrix crystallization screen, which contained 2 M ammonium sulfate, 0.1 M cacodylate buffer pH 6.5 and 0.2 M NaCl). The Fitzgerald's Protein A sample was concentrated to 120 mg/ml as described in "Protein A crystallization in hanging drops" section, and crystal screening was performed in 30 µl microbatches with the above mentioned crystallization reagent. The batches were incubated at room temperature without tumbling during 6 to 15 days. Batch crystallization was also prepared with the recombinant Protein A from Repligen Corporation under the same crystallization conditions. The Protein A crystallization was then scaled up to 0.5 ml batches using Repligen's recombinant Protein A (at either 53 or 120 mg/ml) and in-house formulation #4 of Wizard II crystallization screen. The batches were incubated during 6 days at room temperature. Protein A crystals were also scaled up to 1 ml batches with Repligen's Protein A at 53 mg/ml. The Protein A sample was mixed with in-house formulation #4 of Wizard 11 crystallization screen. The sample was incubated at room temperature with tumbling during 4 weeks.

Cross-Linking of Protein A Crystals.

A 500 µl sample containing 15 mg/ml of Protein A crystals (at 50% slurry in the formulation #4 of the Wizard II screening kit) was cross-linked with 20 µl of glutaraldehyde 25% (the final glutaraldehyde concentration was 1%). The sample was immediately vortexed for 5 seconds, and incubated at room temperature for 20 minutes without agitation. After the incubation, 1 ml of formulation #4 of the Wizard II crystallization screen was added to the sample (final glutaraldehyde concentration was 0.33%), and the complex was vortexed for 5 seconds. The sample was then incubated at room temperature for 1 h without agitation. After cross-linking, the Protein A sample was washed 3 times in 1 ml of 10 mM Tris-HCl buffer pH 7 (centrifugation was carried out at 4,500 rpm for 5 minutes), and the Protein A cross-linked crystals (CLPCs) were resuspended in 1 ml of 10 mM Tris-HCl buffer pH 7.

Results

Hanging-Drop Crystals of Protein A.

Using the hanging-drop crystallization method, Protein A crystals from Fitzgerald International were produced with either a 50.6 or a 120 mg/ml protein sample, and with the formulation #4 of the Wizard II crystallization screen (FIG. 1). Crystals were also produced with the formulation #8 of the Wizard I crystallization screen (2 M ammonium sulfate in citrate buffer pH 5.5), as well as with the following Wizard II crystallization screen formulations: #31 (1 M sodium citrate, 0.1 M Tris-HCl buffer pH 7, 0.2 M NaCl), #35 (0.8 M $NaH_2PO_4$/1.2 M $K_2PO_4$ in 0.1 M acetate buffer pH 4.5) and #41 (2 M ammonium sulfate, Tris-HCl buffer pH 7, 0.2 M lithium sulfate), data not shown. In all the conditions, the crystal size was about 5 microns with a soft cubic shape.

Batch Crystals of Protein A.

Figure 2:
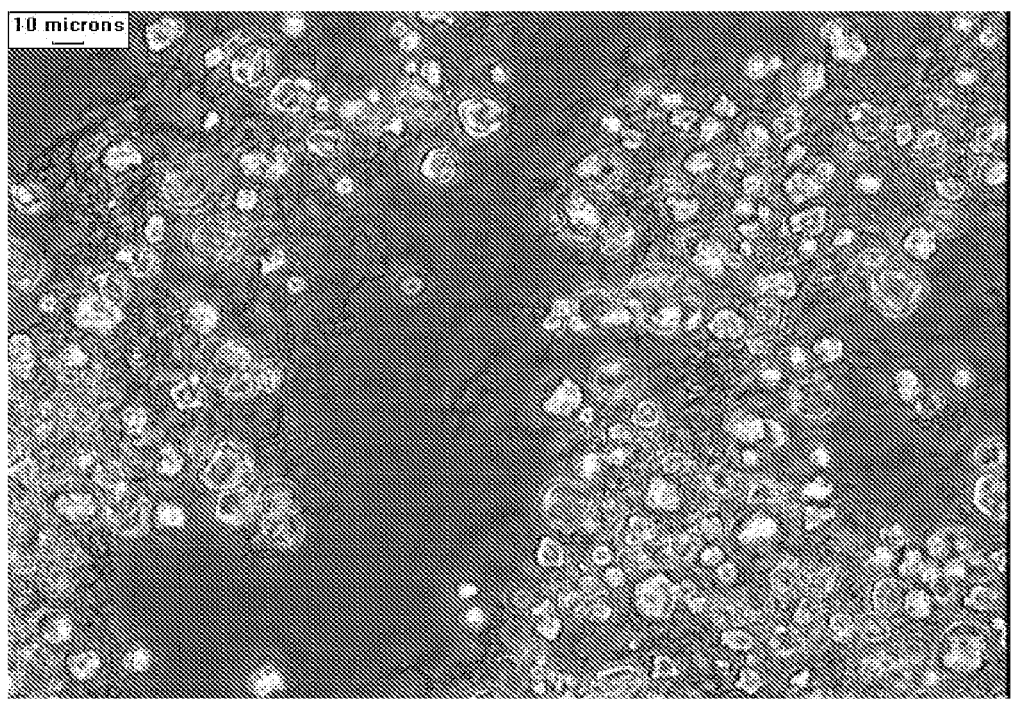
FIG. 2. Protein A crystals in batch. Recombinant Protein A (53 mg/ml in $H_2O$) was crystallized in 1 ml batch with Wizard II crystallization screen.

As shown in FIG. 2, recombinant Protein A from Repligen Corporation was crystallized in 1 ml batches with the formulation #4 of the Wizard II crystallization screen. Crystallization in batches produced both cubic- and needle-shaped crystals. The cubic-shaped crystal size was about 10 microns, while the size of the needles was smaller. Similar crystals were obtained in 30 µl batches with Protein A from both Repligen Corporation and Fitzgerald International, and in 500 µl batches with Repligen's Protein A.

Cross-Linked Protein A Crystals.

Figure 3:
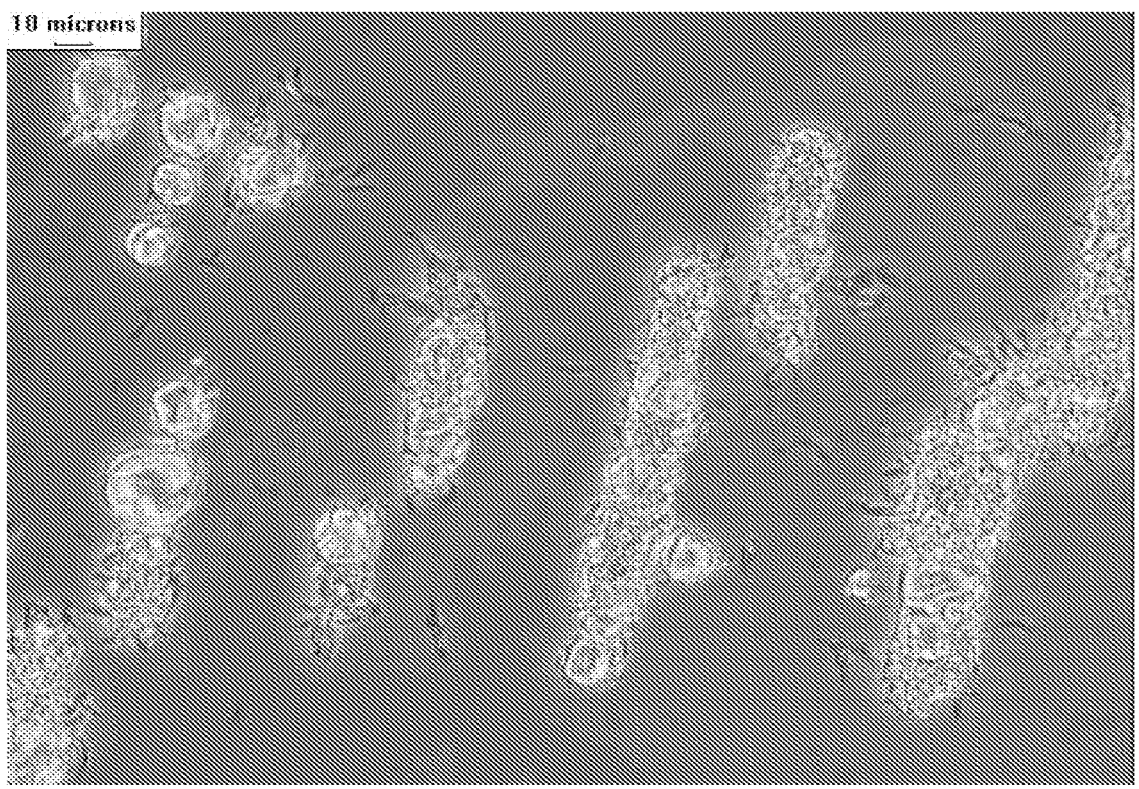
FIG. 3. Cross-linked Protein A crystals. Protein A crystals were cross-linked with glutaraldehyde 1% for 20 minutes and 0.33% for 1 hour.

Protein A crystals from Repligen Corporation were cross-linked with the cross-linker glutaraldehyde. Cross-linking of the Protein A crystals did not change the morphology or the size of the crystals (FIG. 3).

REFERENCES

Crystal Growth 101 Literature, Hanging Drop Vapor Diffusion Crystallization (2001), Hampton Research Corporation.

Example 2

Leaching: pH Controlled Solubility of Cross-Linked Protein a Crystals

Solubility of various cross-linked Protein A crystals is examined following a decrease in pH from 7.5 to 2.0. The cross-linked crystals are incubated at 1 mg/ml in 50 mM glycine-HCl (pH 2.0). Aliquots are removed after 5 hour incubation at 37° C. with stirring. Soluble protein concentration is measured at $OD_{280}$ nm after separation of the undissolved cross-linked crystals by centrifugation at 2000 rpm and filtration of the supernatant through 0.22 μm filter.

Example 3

Purpose

The purpose of the experiment was to determine the binding capacity of the cross-linked protein A crystals using Human IgG.

Equipment and Materials

Equipments:
Table Top Centrifuge: Eppendorf Centrifuge 5415D
Eppendorf Tubes 1 ml
Vacuum pump
Whatman Filter paper discs: 25 mm Cat#1825025
Balance: Mettler Toledo AG285
Conical Flask Material
Cross-linked Protein A crystals: Made in house
Human IgG: ICN Biomedical, Inc. Cat. #64145
Phosphate Buffered Saline (PBS) tablets: Sigma Cat. #P-4417
Glycine: Fluka #50046
0.1N NaOH: Acros Cat #12419-0010

Procedure

Buffer Preparation

Phosphate Buffered Saline (PBS):
1 tablet was dissolved in 200 ml of distilled water to obtain phosphate buffered saline.

0.2 M Glycine pH 2.0:
7.5 g of glycine was dissolved in 90 ml of water. pH was adjusted to 2.0 with 1N HCl. Volume was made up to 100 ml using DI water. The pH was subsequently checked, and adjusted to 2.0 again if necessary.

Experimental Procedure:

Cross-linked Protein A crystals (CLPCs) used in this experiment were in 10 mM Tris pH 7.0. 50 μl of CLPCs were centrifuged to remove supernatant. The pellet was resuspended in PBS and washed with PBS 3 times to equilibrate CLPCs in PBS for antibody binding.

To 50 μl of CLPCs in PBS, 2 mg of IgG in 100 μl volume was added in a reaction tube. The contents of the tube were gently mixed and incubated for 30 min. at RT. The tube was centrifuged at 4500 rpm for 5 min. The supernatant (flow through) was removed and keep aside for analysis.

The pellet was resuspended in 100 μl of PBS and centrifuged at 4500 rpm for 5 min. The supernatant (wash) was removed and kept aside for analysis. This step was repeated 2 more times for a total 3 washes. The 3 washes with PBS (100 μl×3) were pooled in one tube, for a total wash volume of 300 μl.

The pellet was resuspended in 83 μl of 0.2M glycine pH 2.0. The resuspension was mixed gently and incubated for 10 min. The resuspension was centrifuged at 4500 rpm for 5 min and the supernatant (elute) was kept aside for analysis. This step was repeated 2 more times and the 3 glycine elutions were pooled in one tube (Total elution volume of 249 μl).

After the third elution, the pellet was resuspended in 250 μl of 0.1N NaOH to elute any remaining protein that was not eluted with 0.2M Glycine pH 2.0. The resuspension was incubated for 15 min. and centrifuged at 4500 rpm for 5 min. The supernatant (NaOH regeneration) was kept for analysis.

Absorbance of flow through, wash, elution and NaOH regeneration was read at 280 nm.

The CLPCs pellet was then resuspended in 100 μl of PBS to perform dry weight for determination of amount of protein A used in the experiment.

A Whatman filter paper disc was weighed and the weight was recorded. Filter paper was placed on to the conical flask that was attached to vacuum.

100 μl of CLPCs in PBS was added on the filter paper while the vacuum was on, to drain the liquid in the flask. CLPCs were washed 5 times with water. Filter paper was left on the vacuum for sometime to let it dry and then placed it in oven overnight.

The filter paper was weighed the next day and the amount of CLPCs used in the experiment in milligrams was calculated.

Results

Binding capacity of cross-linked Protein A crystals was calculated as amount of Human IgG bound and eluted per gram of CLPCs. IgG concentration in each step of the experiment is shown in Table 1 below.

TABLE 1

| IgG concentrations in different fractions | |
|---|---|
| | EXPERIMENT 1 |
| IgG Load (mg) | 2.00 |
| Flow through (mg) | 0.410 |
| Wash (mg) | 0.093 |
| Elution (mg) | 1.131 |
| NaOH regeneration (mg) | 0.162 |
| Total | 1.796 |

Binding capacity was calculated from dry weight of CLPCs and Human IgG eluted from the CLPCs using this formula:

$$\text{Binding capacity in mg of Human } IgG/\text{gram of } CLPCs = \frac{\text{Human } IgG \text{ Eluted} \times 1000}{\text{Dry weight of } CLPCs}$$

This data is summarized in Table 2 below.

TABLE 2

| Binding capacity calculations | |
|---|---|
| | EXPERIMENT 1 |
| IgG Eluted (mg) | 1.131 |
| Dry weight of CLPCs (mg) | 0.47 |
| Binding capacity (mg of IgG/Gram of CLPCs) | 2406.38 |

CONCLUSIONS

From these experiments, the binding capacity was calculated to be 2406.38 mg of Human IgG per gram of Cross-linked protein A crystals.

Example 4

Purpose

The purpose of the experiment was to determine the binding capacity of the cross-linked protein A crystals using Human IgG.

Equipment and Materials

Equipments:
Table Top Centrifuge: Eppendorf Centrifuge 5415D
Eppendorf Tubes 1 ml Vacuum pump
Whatman Filter paper discs: 25 mm Cat#1825025
Balance: Mettler Toledo AG285
Conical Flask
Material
Cross-linked Protein A crystals: Made in house
Human IgG: ICN Biomedical, Inc. Cat. #64145
Phosphate Buffered Saline (PBS) tablets: Sigma Cat. #P-4417
Glycine: Fluka I#50046
0.1N NaOH: Acros Cat #12419-0010
Procedure
Buffer Preparation
Phosphate Buffered Saline (PBS):

1 tablet was dissolved in 200 ml of distilled water to obtain phosphate buffered saline.
0.2 M glycine pH 2.0:

7.5 g of glycine was dissolved in 90 ml of water. The pH was adjusted to 2.0 with IN HCl. Volume was made up to 100 ml using DI water. The pH was subsequently checked, and adjusted to 2.0 again if necessary.
Experimental Procedure:

Cross-linked Protein A crystals (CLPCs) used in this experiment were in 10 mM Tris pH 7.0. 50 µl of CLPCs were centrifuged to remove supernatant. The pellet was resuspended in PBS and washed with PBS 3 times to equilibrate CLPCs in PBS for antibody binding.

To 50 µl of CLPCs in PBS, 2 mg of IgG in 100 µl volume was added in a reaction tube. The contents of the tube were gently mixed and incubated for 30 min at RT. The tube was centrifuged at 4500 rpm for 5 min. The supernatant (Flow through) was removed and keep aside for analysis.

The pellet was resuspended in 100 µl of PBS and centrifuged at 4500 rpm for 5 min. The supernatant (wash) was removed and kept aside for analysis. This step was repeated 2 more times for a total 3 washes.

The 3 washes with PBS (100 µl×3) were pooled in one tube, for a total wash volume of 300 µl.

The pellet was resuspended in 83 µl of 0.2M glycine pH 2.0. The resuspension was mixed gently and incubated for 10 min. The resuspension was centrifuged at 4500 rpm for 5 min and the supernatant (elute) was kept aside for analysis. This step was repeated 2 more times and the 3 glycine elutions were pooled in one tube (Total elution volume of 249 µl).

After the third elution, the pellet was resuspended in 250 µl of 0.1N NaOH to elute any remaining protein that was not eluted with 0.2M Glycine pH 2.0. The resuspension was incubated for 15 min. and centrifuged at 4500 rpm for 5 min. The supernatant (NaOH regeneration) was kept for analysis.

Absorbance of flow through, wash, elution and NaOH regeneration was read at 280 nm.

The CLPCs pellet was then resuspended in 100 µl of PBS to perform dry weight for determination of amount of protein A used in the experiment.

A Whatman filter paper disc was weighed and the weight was recorded. Filter paper was placed on to the conical flask that was attached to vacuum.

100 µl of CLPCs in PBS was added on the filter paper while the vacuum was on, to drain the liquid in the flask. CLPCs were washed 5 times with water. Filter paper was left on the vacuum for sometime to let it dry and then placed it in oven overnight.

The filter paper was weighed the next day and the amount of CLPCs used in the experiment in milligrams was calculated.

Results

Binding capacity of cross-linked protein A crystals was calculated as amount of Human IgG bound and eluted per gram of CLPCs. IgG concentration in each step of the experiment is shown in Table 3 below.

TABLE 3

IgG concentrations in different fractions

|  | EXPERIMENT 1 | EXPERIMENT 2 | EXPERIMENT 3 |
|---|---|---|---|
| IgG Load (mg) | 2.00 | 10.00 | 10.00 |
| Flow through (mg) | 1.34 | 8.80 | 9.23 |
| Wash (mg) | 0.24 | 0.64 | 0.42 |
| Elution (mg) | 0.32 | 0.62 | 0.18 |
| NaOH regeneration (mg) |  |  | 0.03 |
| Total | 1.90 | 10.06 | 9.83 |

Binding capacity was calculated from dry weight of CLPCs and Human IgG eluted from the CLPCs using this formula:

$$\text{Binding capacity in mg of Human } IgG/\text{gram of } CLPCs = \frac{\text{Human } IgG \text{ Eluted} \times 1000}{\text{Dry weight of } CLPCs}$$

This data is summarized in Table 4 below.

TABLE 4

Binding capacity calculations

|  | EXPERIMENT 1 | EXPERIMENT 2 | EXPERIMENT 3 |
|---|---|---|---|
| IgG Eluted (mg) | 0.32 | 0.62 | 0.18 |
| Dry weight of CLPCs (mg) | 1.55 | 2.75 | 0.79 |
| Binding capacity (mg of IgG/Gram of CLPCs) | 206.45 | 225.4 | 227.8 |
| Average Binding capacity (mg of IgG/Gram of CLPCs) | 219.86 |  |  |

CONCLUSIONS

From these experiments, average binding capacity was calculated to be 219.86 mg of Human IgG per gram of Cross-linked protein A crystals.

Example 5

Purpose

The purpose of the experiment was to determine the binding capacity of the cross-linked protein A crystals using Human IgG.
Equipment and Materials
Equipments:
Table Top Centrifuge: Eppendorf Centrifuge 5415D
Eppendorf Tubes 1 ml
Vacuum pump
Whatman Filter paper discs: 25 mm Cat#1825025
Balance: Mettler Toledo AG285
Conical Flask
Material
Cross-linked Protein A crystals: Made in house
Human IgG: ICN Biomedical, Inc. Cat. #64145

Phosphate Buffered Saline (PBS) tablets: Sigma Cat. #P-4417
Glycine: Fluka #50046
0.1N NaOH: Acros Cat #12419-0010

Procedure

Buffer Preparation

Phosphate Buffered Saline (PBS):

1 tablet was dissolved in 200 ml of distilled water to obtain phosphate buffered saline.

0.2 M glycine pH 2.0:

7.5 g of glycine was dissolved in 90 ml of water. The pH was adjusted to 2.0 with 1N HCl. The volume was made up to 100 ml using DI water. The pH was subsequently checked and adjusted to 2.0 again if necessary.

Experimental Procedure:

Cross-linked Protein A crystals (CLPCs) used in this experiment were in 10 mM Tris pH 7.0. 50 µl of CLPCs were centrifuged to remove supernatant. The pellet was resuspended in PBS and washed with PBS 3 times to equilibrate CLPCs in PBS for antibody binding.

To 50 µl of CLPCs in PBS, 2 mg of IgG in 100 µl volume was added in a reaction tube. The contents of the tube were gently mixed and incubated for 30 min at RT. The tube was centrifuged at 4500 rpm for 5 min. The supernatant (flow through) was removed and keep aside for analysis.

The pellet was resuspended in 100 µl of PBS and centrifuged at 4500 rpm for 5 min. The supernatant (Wash) was removed and kept aside for analysis. This step was repeated 2 more times for a total 3 washes.

The 3 washes with PBS (100 µl×3) were pooled in one tube, for a total wash volume of 300 µl.

The pellet was resuspended in 83 µl of 0.2M glycine pH 2.0. The resuspension was mixed gently and incubated for 10 min. The resuspension was centrifuged at 4500 rpm for 5 min and the supernatant (elute) was kept aside for analysis. This step was repeated 2 more times and the 3 glycine elutions were pooled in one tube (total elution volume of 249 µl).

After the third elution, the pellet was resuspended in 250 µl of 0.1N NaOH to elute any remaining protein that was not eluted with 0.2M Glycine pH 2.0. The resuspension was incubated for 15 min. and centrifuged at 4500 rpm for 5 min. The supernatant (NaOH regeneration) was kept for analysis.

Absorbance of flow through, wash, elution and NaOH regeneration was read at 280 nm.

The CLPCs pellet was then resuspended in 100 µl of PBS to perform dry weight for determination of amount of protein A used in the experiment.

A Whatman filter paper disc was weighed and the weight was recorded. Filter paper was placed on to the conical flask that was attached to vacuum.

100 µl of CLPCs in PBS was added on the filter paper while the vacuum was on, to drain the liquid in the flask. CLPCs were washed 5 times with water. Filter paper was left on the vacuum for sometime to let it dry and then placed it in oven overnight.

The filter paper was weighed the next day and the amount of CLPCs used in the experiment in milligrams was calculated.

Results

Binding capacity of cross-linked protein A crystals was calculated as amount of Human IgG bound and eluted per gram of CLPCs. IgG concentration in each step of the experiment is shown in Table 5 below.

TABLE 5

IgG concentrations in different fractions

| | EXPERIMENT 1 |
|---|---|
| IgG Load (mg) | 2.00 |
| Flow through (mg) | 1.066 |
| Wash (mg) | 0.179 |
| Elution (mg) | 0.592 |
| NaOH regeneration (mg) | 0.109 |
| Total | 1.946 |

Binding capacity was calculated from dry weight of CLPCs and Human IgG eluted from the CLPCs using this formula:

$$\text{Binding capacity in mg of Human } IgG/\text{gram of } CLPCs = \frac{\text{Human } IgG \text{ Eluted} \times 1000}{\text{Dry weight of } CLPCs}$$

This data is summarized in Table 6 below.

TABLE 6

Binding capacity calculations

| | EXPERIMENT 1 |
|---|---|
| IgG Eluted (mg) | 0.592 |
| Dry weight of CLPCs (mg) | 0.55 |
| Binding capacity (mg of IgG/Gram of CLPCs) | 1076.4 |

CONCLUSIONS

From these experiments, the binding capacity was calculated to be 1076.4 mg of Human IgG per gram of Cross-linked protein A crystals.

Example 6

This Example describes the determination of human immunoglobulin G (IgG) binding capacity of Protein A CLPCs in both batches and columns.

Equipment and Materials

5415C Centrifuge: Eppendorf International, Inc.

Ultrafree®-MC centrifugal filter units: Durapore® PVDF 0.2 □m, Millipore

Glass microfiber filter: Whatman, Schleicher & Schuell, Cat. No. 1825-025

Empty Sep-Pak® Vac column: Waters Corporation pH conductivity meter: Denver Instrument, Model 220

8453 UV-Visible Spectrophotometer: Agilent Technologies

Protein A cross-linked crystals: produced using Altus' proprietary technology

DI (Reverse Osmosis & De-Ionization) H$_2$O

Hydrochloric Acid Solution, 1N Certified: Fisher Scientific, Cat. No. SA48-1

Sodium Hydroxide Solution N/2, 0.5 N: Fisher Scientific, Cat. No. SS270-1

Sodium hydroxide Solution, 1N Certified: Fisher Scientifics, Cat. No. SS266-1

Phosphate buffered saline tablets: Sigma-Aldrich, Cat. No. P-4417

Citric acid anhydrous: Fisher Scientific, Cat. No. A940-1

Glycine: Fisher Scientific, Cat. No. G48-500

Tris (hydroxymethyl) aminomethane (Trizma Base): Sigma-Aldrich, Cat. No. T-4661

Procedure

Solution Preparation

Phosphate Buffered Saline Solution

One phosphate buffered saline (PBS) tablet from Sigma-Aldrich was dissolved in 200 ml DI $H_2O$, so as to prepare the following PBS solution: 0.01 M phosphate buffer, 2.7 mM KCl, 137 mM NaCl at pH 7.4.

1 M Tris-HCl Buffer pH 8.5

12.11 g of Trizma Base was dissolved in 80 ml DI $H_2O$. The pH was adjusted to 8.5 with 1 N HCl solution, and the solution was adjusted to 100 ml with DI $H_2O$.

0.2 M glycine buffer pH 2

1.5 g of glycine was dissolved in 80 ml DI $H_2O$. The pH was adjusted to 2 with 1 N HCl solution, and the solution was adjusted to 100 ml with DI $H_2O$.

0.1 M citric acid buffer pH 3

1.9 g of citric acid anhydrous was dissolved in 80 ml DI $H_2O$. The pH was adjusted to 3 with 1 N NaOH solution, and the solution was adjusted to 100 ml with DI $H_2O$.

0.1 N NaOH solution 100 ml of 0.5 N NaOH solution was diluted with 400 ml DI $H_2O$.

Human IgG Binding Capacity of Protein a CLPCs

Determination of IgG Binding Capacity in Columns

An empty Waters Sep-Pak® Vac column was packed with Protein A CLPCs (the bed volume was approximately 500 µl with a Protein A CLPC).

The column was equilibrated with 5 ml PBS, and loaded with 2000 mg of human IgG from ICN Biomedicals at a concentration of 20 mg/ml in PBS.

The flow-through was collected in 10 ml aliquots, and the protein concentration was determined by spectrophotometry at 280 nm.

The column was then washed with 5 ml PBS, and 1 ml fractions were collected.

Human IgG was eluted with 5 ml of 0.2 M glycine buffer pH 2, and the glycine eluate was collected in 1 ml aliquots and assayed for protein concentration by spectrophotometry at 280 nm. Each eluted fraction was adjusted to physiologic pH with 100 µl of 1 M Tris-HCl buffer pH 8.5.

After the glycine elution, the column was regenerated with 5 ml of 0.1 M citric acid/NaOH buffer pH 3, which was collected after its elution from the column.

Finally, the column was cleaned with 3 ml of 0.1 M NaOH solution. Fractions of 1 ml were collected and the column was washed with 5 mil PBS.

After the A280 spectrophotometric assays, the flow-through fractions, as well as the fractions of the PBS washes and of the NAOH washes were pooled separately.

Results

Binding capacity of cross-linked protein A crystals was calculated as amount of Human IgG bound and eluted per gram of CLPCs. IgG concentration in each step of the experiment is shown in Table 7 below.

TABLE 7

IgG concentrations in different fractions

|  | EXPERIMENT 1 |
|---|---|
| IgG Load (mg) | 2000 |
| Flow through (mg) | 1445.51 |
| Wash (mg) | 439.3 |

TABLE 7-continued

IgG concentrations in different fractions

|  | EXPERIMENT 1 |
|---|---|
| Elution (mg) | 75.1 |
| NaOH regeneration (mg) | 0.0 |
| Total | 1959.91 |

Binding capacity was calculated from dry weight of CLPCs and Human IgG eluted from the CLPCs using this formula:

$$\text{Binding capacity in mg of Human } IgG/\text{gram of } CLPCs = \frac{\text{Human } IgG \text{ Eluted} \times 1000}{\text{Dry weight of } CLPCs}$$

This data is summarized in Table 8 below.

TABLE 8

Binding capacity calculations

|  | EXPERIMENT 1 |
|---|---|
| IgG Eluted (mg) | 75.1 |
| Dry weight of CLPCs (mg) | 389.4 |
| Binding capacity (mg of IgG/Gram of CLPCs) | 192.86 |

CONCLUSIONS

From these experiments, binding capacity was calculated to be 192.86 mg of Human IgG per gram of Cross-linked Protein A crystals or 150.2 mg/mL of Protein A column.

A number of embodiments of the invention have been described. Nevertheless, it will be understood that various modifications may be made without departing from the spirit and scope of the invention. Accordingly, other embodiments are within the scope of the following claims.

Experiment No. 7

In this experiment, the effects of post treatment on binding capacity of the Protein A-CLPC are evaluated. The Protein A-CLPC impregnated membranes are made by forming a membrane casting solution with polyurethane in a specific type of solvent; adding Protein A-CLPC to the casting solution; precipitating an impregnated membrane composite material in a suitable media; and optionally processing the composite material by drying prior to use. Specific processing conditions, such as the type of membrane casting solvent e.g. DMF, amount of Protein A-CLPC, precipitation bath media (50/50 IPA/water) and post treatment conditions (wet never dried), for each of the test impregnated membranes are identified and are tested. The Protein A-CLPC binding capacity is tested for each of the test impregnated membranes.

Experiment No. 8

In this experiment, two groups of test impregnated membranes are made, namely Groups A and B. Group A membranes (e.g., A1-A2) are made from polyurethane in a NMP solvent. Group B membranes (e.g., B1-B2) are made from polyurethane in a DMF solvent. The impregnated membranes are about 1 inch in diameter. Specific processing conditions, such as the type of membrane casting solvent e.g. DMF or NMP, amount of Protein A-CLPC, precipitation bath media (50/50 IPA/water or water alone) and post treatment conditions (wet never dried or 40% glycerol dried), exposure to gamma radiation (15 to 40 kGy) for each of the test impregnated membranes are identified and are tested. Once formed, a membrane from each group is exposed to gamma radiation at certain dosages. The other membrane in each group is used as a control with no exposure to gamma-radiation. The antibody binding capacity of each of the membranes is then tested with a antibody test solution. The results will provide the retention of the binding capacity and stability to organic solvents and gamma-radiation exposure of Protein A-CLPC. Sequences:

The cDNA sequence of Protein A from *Staphylococcus aureus* is shown below (GenBank Accession Number: X61307) (SEQ ID NO:1).

```
   1 atgatgactt tacaaataca tacaggsggt attaatttga aaaagaaaaa catttattca
  61 attcgtaaac taggtgtagg tattgcatct gtaactttag gtacattact tatatctggt
 121 ggcgtaacac ctgctgcaaa tgctgcgcaa cacgatgaag ctcaacaaaa tgcttttat
 181 caagtgttaa atatgcctaa cttaaacgct gatcaacgta atggttttat ccaaagcctt
 241 aaagatgatc caagccaaag tgctaacgtt ttaggtgaag ctcaaaaact taatgactct
 301 caagctccaa aagctgatgc gcaacaaaat aagttcaaca aagatcaaca aagcgccttc
 361 tatgaaatct tgaacatgcc taacttaaac gaagagcaac gcaatggttt cattcaaagt
 421 cttaaagacg atccaagcca aagcactaac gttttaggtg aagctaaaaa attaaacgaa
 481 tctcaagcac cgaaagctga caacaatttc aacaaagaac aacaaaatgc tttctatgaa
 541 atcttgaaca tgcctaactt gaacgaagaa caacgcaatg gtttcatcca agcttaaaa
 601 gatgacccaa gtcaaagtgc taacccttta gcagaagcta aaagctaaa tgatgcacaa
 661 gcaccaaaag ctgacaacaa attcaacaaa gaacaacaaa atgctttcta tgaaatttta
 721 catttaccta acttaactga gaacaacgt aacggcttca tccaaagcct taaagacgat
 781 ccttcagtga gcaaagaaat tttagcagaa gctaaaaagc taaacgatgc tcaagcacca
 841 aaagaggaag acaacaacaa gcctggcaaa gaagacaaca acaagcctgg taaagaagac
 901 ggcaacaaac ctggtaaaga agacaacaaa aaacctggca agaagacgg caacaaacct
 961 ggtaaagaag acaacaaaaa acctggtaaa gaagatggca acaaacctgg taaagaagac
1021 ggcaacaagc ctggtaaaga agatggcaac aagcctggta agaagacgg caacggagta
1081 catgtcgtta aacctggtga tacagtaaat gacattgcaa aagcaaacgg cactactgct
1141 gacaaaattg ctgtagataa caaattagct gataaaaaca tgatcaaacc tggtcaagaa
1201 cttgttgttg ataagaagca accagcaaac catgcagatg ctaacaaagc tcaagcatta
1261 ccagaaactg gtgaagaaaa tccattcatc ggtacaactg tatttggtgg attatcatta
1321 gcgttaggtg cagcgttatt agctggacgt cgtcgcgaac tataa
```

The translated Protein A protein from *Staphylococcus aureus* sequence is shown below (GenBank Accession Number: CAA43604) (SEQ ID NO:2).

```
  1 mmtlqihtgg inlkkkniys irklgvgias vtlgtllisg gvtpaanaaq hdeaqqnafy
 61 qvlnmpnlna dqrngfiqsl kddpsqsanv lgeaqklnds qapkadaqqn kfnkdqqsaf
121 yeilnmpnln eeqrngfiqs lkddpsqstn vlgeakklne sqapkadnnf nkeqqnafye
181 ilnmpnlnee qrngfiqslk ddpsqsanll aeakklndaq apkadnkfnk eqqnafyeil
241 hlpnlteeqr ngfiqslkdd psvskeilae akklndaqap keednnkpgk ednnkpgked
301 gnkpgkednk kpgkedgnkp gkednkkpgk edgnkpgked gnkpgkedgn kpgkedgngv
361 hvvkpgdtvn diakangtta dkiavdnkla dknmikpgqe lvvdkkqpan hadankaqal
421 petgeenpfi gttvfgglsl algaallagr rrel
```

What is claimed is:

1. A method of purifying an immunoglobulin comprising contacting said immunoglobulin using a composition comprising cross-linked crystalline (CLCP) form of Protein A.

2. The method of claim 1, wherein said immunoglobulin is an antibody.

3. The method of claim 2, wherein said antibody is a therapeutic antibody.

4. The method of claim 2, wherein said antibody is a monoclonal antibody.

5. The method of claim 1, wherein said immunoglobulin is a Fab fragment.

6. The method of claim 1, wherein said immunoglobulin is an Fc fragment.

7. The method of claim 1, wherein said immunoglobulin is a single chain antibody.

8. The method of claim 1, wherein said immunoglobulin is a chimeric antibody.

9. The method of claim 1, wherein said immunoglobulin is a fully human antibody.

10. The method of claim 1, wherein said immunoglobulin is a humanized antibody.

11. The method of claim 1, wherein said immunoglobulin belongs to class IgG.

12. The method of claim 1, wherein said composition comprises cross-linked crystalline form of Protein A, wherein the composition is cross-linked with glutaraldehyde.

13. A process for the purification of immunoglobulins which comprises:
   (a) mixing a medium containing immunoglobulins with a buffer solution having a pH in the range of about pH 7.0 to pH 10 and containing a combination of cations and anions to provide a buffered immunoglobulin medium;
   (b) contacting said buffered immunoglobulin medium with an immobilized cross-linked crystalline (CLCP) form of Protein A adsorbent to adsorb the immunoglobulins present in said buffered immunoglobulin medium upon said immobilized CLPC adsorbent;
   (c) washing the CLPC adsorbent having immunoglobulins adsorbed thereon with said buffer solution;
   (d) contacting said CLPC adsorbent having immunoglobulins adsorbed thereon with a buffer solution having a pH in the range of about pH 2 to pH 6 to remove the adsorbed immunoglobulins from the CLPC adsorbent; and
   (e) recovering the removed immunoglobulins in substantially pure form.

14. The process according to claim 13, wherein the contacting of said buffered immunoglobulin medium with said CLPC adsorbent is accomplished in a column of said CLPC adsorbent.

15. The process according to claim 13, wherein said medium containing immunoglobulins is a normal mammalian serum.

16. The process according to claim 13, wherein said medium containing immunoglobulins is an immune mammalian serum.

17. The process according to claim 13, wherein said medium is a mammalian plasma.

18. The process according to claim 13, wherein said medium is mammalian ascites fluid.

19. The process according to claim 13, wherein said medium is obtained from a hybridoma.

20. The process according to claim 13, wherein said medium is a tissue culture fluid.

21. The process according to claim 13, wherein said medium is a cell culture fluid.

22. The process according to claim 13, wherein said medium is a mammalian cell culture fluid.

23. The process according to claim 13, wherein said medium is a bacterial cell culture fluid.

24. The process according to claim 13, wherein said medium is a transgenic source fluid.

25. The process according to claim 13, wherein said medium is a plant extract containing immunoglobulins.

26. The process according to claim 13, wherein said medium is a yeast culture fluid.

27. A method of purification comprising contacting the substance to be purified with a composition comprising cross-linked crystalline form of Protein A.

28. The method of claim 1, wherein Protein A within said CLPC is Protein A polypeptide or polypeptide fragments of Protein A.

29. The method of claim 28, wherein Protein A and fragments thereof bind at least one immunoglobulin at the Fc-part.

30. The method of claim 1 wherein the Protein A is derived from *Staphylococcus* sp.

31. The method of claim 30, wherein said *Staphylococcus* is *Staphylococcus aureus* or *Staphylococcus epidermidis*.

32. The method of claim 1, wherein the cross-linking of the Protein A crystals comprises covalent links between the constituent protein molecules of the crystal.

33. The method of claim 30, wherein the cross-linking of the Protein A crystals is through lysine amine groups, thiol groups and carbohydrate moieties.

34. The process according to claim 13, wherein, wherein said CLPC is insoluble in said medium.

* * * * *

SEQUENCE LISTING

<160> NUMBER OF SEQ ID NOS: 2

<210> SEQ ID NO 1
<211> LENGTH: 1365
<212> TYPE: DNA
<213> ORGANISM: Staphylococcus aureus
<220> FEATURE:
<223> OTHER INFORMATION: cDNA sequence of Protein A from Staphylococcus aureus

<400> SEQUENCE: 1

```
atgatgactt tacaaataca tacaggggt attaatttga aaagaaaaa catttattca        60
attcgtaaac taggtgtagg tattgcatct gtaactttag gtacattact tatatctggt      120
ggcgtaacac ctgctgcaaa tgctgcgcaa cacgatgaag ctcaacaaaa tgctttttat     180
caagtgttaa atatgcctaa cttaaacgct gatcaacgta atggttttat ccaaagcctt     240
aaagatgatc caagccaaag tgctaacgtt ttaggtgaag ctcaaaaact taatgactct     300
caagctccaa agctgatgc gcaacaaaat aagttcaaca aagatcaaca aagcgccttc      360
tatgaaatct tgaacatgcc taacttaaac gaagagcaac gcaatggttt cattcaaagt     420
cttaaagacg atccaagcca agcactaac gttttaggtg aagctaaaaa attaaacgaa      480
tctcaagcac cgaaagctga caacaatttc aacaaagaac aacaaaatgc tttctatgaa     540
atcttgaaca tgcctaactt gaacgaagaa caacgcaatg gtttcatcca aagcttaaaa     600
gatgacccaa gtcaaagtgc taaccttta gcagaagcta aaagctaaa tgatgcacaa      660
gcaccaaaag ctgacaacaa attcaacaaa gaacaacaaa atgctttcta tgaaattta     720
catttaccta acttaactga gaacaacgt aacggcttca tccaaagcct taaagacgat     780
ccttcagtga gcaaagaaat tttagcagaa gctaaaaagc taaacgatgc tcaagcacca     840
aaagaggaag acaacaacaa gcctggcaaa gaagacaaca caagcctgg taaagaagac      900
ggcaacaaac ctggtaaaga agacaacaaa aaacctggca agaagacgg caacaaacct       960
ggtaaagaag acaacaaaaa acctggtaaa gaagatggca caaacctgg taaagaagac      1020
ggcaacaagc tggtaaaga gatggcaac aagcctggta agaagacgg caacggagta       1080
catgtcgtta aacctggtga tacagtaaat gacattgcaa agcaaacgg cactactgct     1140
gacaaaattg ctgtagataa caaattagct gataaaaaca tgatcaaacc tggtcaagaa     1200
cttgttgttg ataagaagca accagcaaac catgcagatg ctaacaaagc tcaagcatta     1260
ccagaaactg tgaagaaaa tccattcatc ggtacaactg tatttggtgg attatcatta     1320
gcgttaggtg cagcgttatt agctggacgt cgtcgcgaac tataa                     1365
```

<210> SEQ ID NO 2
<211> LENGTH: 454
<212> TYPE: PRT
<213> ORGANISM: Staphylococcus aureus
<220> FEATURE:
<223> OTHER INFORMATION: Translated Protein A from Staphylococcus aureus

<400> SEQUENCE: 2

```
Met Met Thr Leu Gln Ile His Thr Gly Gly Ile Asn Leu Lys Lys Lys
 1               5                  10                  15

Asn Ile Tyr Ser Ile Arg Lys Leu Gly Val Gly Ile Ala Ser Val Thr
             20                  25                  30

Leu Gly Thr Leu Leu Ile Ser Gly Gly Val Thr Pro Ala Ala Asn Ala
         35                  40                  45

Ala Gln His Asp Glu Ala Gln Gln Asn Ala Phe Tyr Gln Val Leu Asn
```

```
                50              55              60
        Met Pro Asn Leu Asn Ala Asp Gln Arg Asn Gly Phe Ile Gln Ser Leu
        65              70              75              80

Lys Asp Asp Pro Ser Gln Ser Ala Asn Val Leu Gly Glu Ala Gln Lys
                        85              90              95

Leu Asn Asp Ser Gln Ala Pro Lys Ala Asp Ala Gln Gln Asn Lys Phe
                        100             105             110

Asn Lys Asp Gln Gln Ser Ala Phe Tyr Glu Ile Leu Asn Met Pro Asn
                        115             120             125

Leu Asn Glu Glu Gln Arg Asn Gly Phe Ile Gln Ser Leu Lys Asp Asp
                        130             135             140

Pro Ser Gln Ser Thr Asn Val Leu Gly Glu Ala Lys Lys Leu Asn Glu
        145             150             155             160

Ser Gln Ala Pro Lys Ala Asp Asn Asn Phe Asn Lys Glu Gln Gln Asn
                        165             170             175

Ala Phe Tyr Glu Ile Leu Asn Met Pro Asn Leu Asn Glu Glu Gln Arg
                        180             185             190

Asn Gly Phe Ile Gln Ser Leu Lys Asp Asp Pro Ser Gln Ser Ala Asn
                        195             200             205

Leu Leu Ala Glu Ala Lys Lys Leu Asn Asp Ala Gln Ala Pro Lys Ala
                        210             215             220

Asp Asn Lys Phe Asn Lys Glu Gln Gln Asn Ala Phe Tyr Glu Ile Leu
        225             230             235             240

His Leu Pro Asn Leu Thr Glu Glu Gln Arg Asn Gly Phe Ile Gln Ser
                        245             250             255

Leu Lys Asp Asp Pro Ser Val Ser Lys Glu Ile Leu Ala Glu Ala Lys
                        260             265             270

Lys Leu Asn Asp Ala Gln Ala Pro Lys Glu Glu Asp Asn Asn Lys Pro
                        275             280             285

Gly Lys Glu Asp Asn Asn Lys Pro Gly Lys Glu Asp Gly Asn Lys Pro
                        290             295             300

Gly Lys Glu Asp Asn Lys Lys Pro Gly Lys Glu Asp Gly Asn Lys Pro
        305             310             315             320

Gly Lys Glu Asp Asn Lys Lys Pro Gly Lys Glu Asp Gly Asn Lys Pro
                        325             330             335

Gly Lys Glu Asp Gly Asn Lys Pro Gly Lys Glu Asp Gly Asn Lys Pro
                        340             345             350

Gly Lys Glu Asp Gly Asn Gly Val His Val Val Lys Pro Gly Asp Thr
                        355             360             365

Val Asn Asp Ile Ala Lys Ala Asn Gly Thr Thr Ala Asp Lys Ile Ala
        370             375             380

Val Asp Asn Lys Leu Ala Asp Lys Asn Met Ile Lys Pro Gly Gln Glu
        385             390             395             400

Leu Val Val Asp Lys Lys Gln Pro Ala Asn His Ala Asp Ala Asn Lys
                        405             410             415

Ala Gln Ala Leu Pro Glu Thr Gly Glu Glu Asn Pro Phe Ile Gly Thr
                        420             425             430

Thr Val Phe Gly Gly Leu Ser Leu Ala Leu Gly Ala Ala Leu Leu Ala
                        435             440             445

Gly Arg Arg Arg Glu Leu
        450
```